United States Patent
Hong et al.

(10) Patent No.: US 9,334,230 B2
(45) Date of Patent: May 10, 2016

(54) PROCESS OF FORMING AN AMIDE

(75) Inventors: Soon Hyeok Hong, Singapore (SG); Subhash Chandra Ghosh, Singapore (SG); Yao Zhang, Singapore (SG); Senthilkumar Muthaiah, Singapore (SG); Cheng Chen, Singapore (SG); Xiangya Xu, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 419 days.

(21) Appl. No.: 13/496,466

(22) PCT Filed: Sep. 20, 2010

(86) PCT No.: PCT/SG2010/000351
§ 371 (c)(1),
(2), (4) Date: May 21, 2012

(87) PCT Pub. No.: WO2011/034506
PCT Pub. Date: Mar. 24, 2011

(65) Prior Publication Data
US 2012/0220768 A1    Aug. 30, 2012

Related U.S. Application Data

(60) Provisional application No. 61/243,803, filed on Sep. 18, 2009.

(51) Int. Cl.
| | |
|---|---|
| *C07F 15/00* | (2006.01) |
| *C07C 231/10* | (2006.01) |
| *C07D 207/267* | (2006.01) |
| *C07D 211/76* | (2006.01) |
| *C07D 223/10* | (2006.01) |
| *C07D 295/185* | (2006.01) |
| *C07D 295/192* | (2006.01) |
| *B01J 31/22* | (2006.01) |

(52) U.S. Cl.
CPC ........... *C07C 231/10* (2013.01); *B01J 31/2269* (2013.01); *C07D 207/267* (2013.01); *C07D 211/76* (2013.01); *C07D 223/10* (2013.01); *C07D 295/185* (2013.01); *C07D 295/192* (2013.01); *C07F 15/0046* (2013.01); *B01J 2231/763* (2013.01); *B01J 2531/821* (2013.01)

(58) Field of Classification Search
CPC ............................ C07F 15/0046; C07C 231/10
See application file for complete search history.

(56) References Cited

U.S. PATENT DOCUMENTS

2009/0112005 A1    4/2009    Milstein et al.

FOREIGN PATENT DOCUMENTS

WO    2010/058004 A1    5/2010

OTHER PUBLICATIONS

Ghosh et al. "Direct Amide Synthesis from Alcohols and Amines by Phosphine-Free Ruthenium Catalyst Systems" Adv. Synth. Catal., 2009, vol. 351, pp. 2643-2649.*
Ali et al., "Catalytic and regioselective synthesis of gem- or trans-α, β-unsaturated amides by carbonylation of alkyl alkynes with aniline derivatives by palladium (II) and phosphine," *Applied Organometallic Chemistry* 17:921-931, 2003.
Beller et al., "Progress in hydroformylation and carbonylation," *Journal od Molecular Catalysis A: 104*:17-85, 1995.
Chang et al., "Highly Efficient Ruthenium(II) Porphyrin Catalyzed Amidation of Aldehydes," *Agnew. Chem. Int. Ed. 47*:1138-1140, 2008.
Cho et al., "Copper-Catalyzed Hydrative Amide Synthesis with Terminal Alkyne, Sulfonyl Azide, and Water," *J. Am. Chem. Soc. 127*:16046-16047, 2005.
Chu et al., "An Acidity Scale of 1,3-Dialkylimidazolium Salts in Dimethyl Sulfoxide Solution," *J. Org. Chem. 72*:7790-7793, 2007.
Damkaci et al., "Stereoselective Synthesis of α- and β-glycosylamide Derivatives from Glycopyranosyl Azides via Isoxazoline Intermediates," *J. Am. Chem. Soc. 125*:4408-4409, 2003.
Demerseman et al., "Direct Preparation of [Ru($\eta^2$-$O_2$CO)($\eta^6$-16-arene)] Carbonate Complexes (L = Phosphane, Carbene) and Their Use as Precursors of [Ru$H_2$(p-cymene)(P$Cy_3$)] and [Ru($\eta^6$-arene)(L)(MeCN)$_2$][B$F_4$]$_2$: X-ray Crystal Structure Determination of [Ru($\eta^2$-$O_2$CO)(p-cymene)(P$Cy_3$)]•1/2C$H_2$C$l_2$ and [Ru($\eta^2$-$O_2$CO)($\eta^6$-$C_6$M$e_6$)-(PM$e_3$)]•$H_2$O," *Eur. J. Inorg. Chem.*, pp. 1174-1181, 2006.

(Continued)

*Primary Examiner* — Joseph Kosack
(74) *Attorney, Agent, or Firm* — Seed IP Law Group PLLC

(57) ABSTRACT

A process is provided for the synthesis of an amide. A primary or secondary amine and a primary alcohol, with the amine and the alcohol being either moieties of different reactants or moieties of the same molecule, are contacted in the presence of a Ruthenium (II) catalyst. The Ruthenium (II) catalyst is free of a phosphine ligand. The process is also carried out in the absence of a phosphine. Providing the Ruthenium (II) catalyst includes providing an N-heterocyclic carbene.

5 Claims, 8 Drawing Sheets

(56) References Cited

OTHER PUBLICATIONS

Eguillor et al., "Abnormal and Normal N-Heterocyclic Carbene Osmium Polyhydride Complexes Obtained by Direct Metalation of Imidazolium Salts," *Organometallics* 27:445-450, 2008.

Gololobov et al., "Tetrahedron Report No. 307: Recent Advances in the Staudinger Reaction," *Tetrahedron* 48(8):1353-1406, 1992.

Ghosh et al., "Direct Amide Synthesis from Alcohols and Amines by Phosphine-Free Ruthenium Catalyst Systems," *Adv. Synth. Catal.* 351:2643-2649, 2009.

Ghosh et al., "Simple $RuCl_3$-Catalyzed Amide Synthesis from Alcohols and Amines," *Eur. J. Org. Chem.*, pp. 4266-4270, 2010.

Gunanathan et al., "Direct Synthesis of Amides from Alcohols and Amines with Liberation of $H_2$," *Science* 317:790-792, 2007.

Hahn et al., "Heterocyclic Carbenes: Synthesis and Coordination Chemistry," *Angew. Chem. Int. Ed.* 47:3122-3172, 2008.

Hamid et al., "Ruthenium-Catalyzed N-Alkylation of Amines and Sulfonamides Using Borrowing Hydrogen Methodology," *J. Am. Chem. Soc.* 131:1766-1774, 2009.

Han et al., "Recent development of peptide coupling reagents in organic synthesis," *Tetrahedron* 60:2447-2467, 2004.

Hashimoto et al., "Beckmann Rearrangement of Ketoximes to Lactams by Triphosphazene Catalyst," *J. Org. Chem.* 73:2894-2897, 2008.

Herrmann et al., "N-Heterocyclic Carbenes[+]: Generation under Mild Conditions and Formation of Group 8-10 Transition Metal Complexes Relevant to Catalysis," *Chem. Eur. J.* 2(7):772-780, 1996.

Humphrey et al., "Chemical Synthesis of Natural Product Peptides: Coupling Methods for the Incorporation of Noncoded Amino Acids into Peptides," *Chem. Rev.* 97:2243-2266, 1997.

Khramov et al., "N-Heterocyclic Carbene—Transition Metal Complexes: Spectroscopic and Crystallographic Analyses of π-Backbonding Interactions," *Organometallics* 26:6042-6049, 2007.

Kirmse, "Stable Singlet Carbenes-Plentiful and Versatile," *Angew. Chem. Int. Ed* 43:1767-1769, 2004.

Knapton et al., "The Regio- and Stereoselective One-Pot Catalytic Preparation β-Selenyl Acrylamides," *Organic Letters* 6(5):687-689, 2004.

Kolakowski et al., "Mechanism of Thio Acid/Azide Amidation," *J. Am. Chem. Soc.* 128:5695-5702, 2006.

Kühl, "The chemistry of functionalized N-heterocyclic carbenes," *Chem. Soc. Rev.* 36:592-607, 2007.

Lang et al., "Azide rearrangements in electron-deficient systems," *Chem. Soc. Rev.* 35:146-156, 2006.

Lo et al., "Simple Ruthenium Precatalyst for the Synthesis of Stilbene Derivatives and Ring-Closing Metathesis in the Presence of Styrene Initiators," *Adv. Synth. Catal.* 349:546-550, 2007.

Martinelli et al., "Palladium-Cataylzed Aminocarbonylation of Aryl Chlorides at Atmospheric Pressure: The Dual Role of Sodium Phenoxide," *Angew. Chem. Int. Ed.* 46:8460-8463, 2007.

Montalbetti et al., "Amide bond formation and peptide coupling," *Tetrahedron* 61:10827-10852, 2005.

Nanayakkara et al., "Asymmetric synthesis of α-aminoamides by Pd-catalyzed double carbohydroamination," *Chem. Commun.*, pp. 2384-2385, 2003.

Naota et al., "Ruthenium-Catalyzed Transformations of Amino Alcohols to Lactams," *Synlett*, pp. 693-694, Sep. 1991.

Nordstrøm et al., "Amide Synthesis from Alcohols and Amines by the Extrusion of Dihydrogen," *J. Am. Chem. Soc.* 130:17672-17673, 2008.

Owston et al., "Highly Efficient Ruthenium-Catalyzed Oxime to Amide Rearrangement," *Organic Letters* 9(18):3599-3601, 2007.

Park et al., "Cobalt-Rhodium Heterobimetallic Nanoparticle-Catalyzed Synthesis of α,β-Unsaturated Amides from Internal Alkynes, Amines and Carbon Monoxide," *Organic Letters* 9(13), 2007.

Pianowski et al., "Imaging of mRNA in Live Cells Using Nucleic Acid-Templated Reduction of Azidorhodamine Probes," *J. Am. Chem. Soc.* 131:6492-6497, 2009.

Ribelin et al., "Highly Stereoselective Ring Expansion Reactions Mediated by Attractive Cation-n Interaction," *Angew. Chem. Int. Ed.* 47:6233-6235, 2008.

Saxon et al., "Cell Surface Engineering by a Modified Staudinger Reaction," *Science* 287:2007-2010, 2000.

Shimizu et al., "Direct Dehydrogenative Amide Synthesis from Alcohols and Amines Catalyzed by γ-Alumina Supported Silver Cluster," *Chem. Eur. J.* 15:9977-9980, 2009.

Starikova et al., "Synthesis of 1,2-Dialkylimidazolium and 1,3-Dialkylbenzimidazolium Salts," *Russian Journal of Organic Chemistry* 39(10):1467-1470, 2003.

Tillack et al., "Catalytic Amination of Aldehydes to Amides," *Eur. J. Org. Chem.*, pp. 523-528, 2001.

Uenoyama et al., "Alkyne Carbonylation by Radicals: Tin-Radical-Catalyzed Synthesis of α-Methylene Amides from 1-Alkynes, Carbon Monoxide, and Amines," *Angew. Chem. Int. Ed.* 44:1075-1078, 2005.

Valeur et al., "Amide bond formation: beyond the myth of coupling reagents," *Chem. Soc. Rev.* 38:606-631, 2009.

Watanabe et al., "Ruthenium-Catalyzed N-Alkyation and N-Benzylation of Aminoarenes with Alcohols," *J. Org. Chem.* 49:335-3363, 1984.

Watson et al., "Ruthenium-Catalyzed Oxidation of Alcohols into Amides," *Organic Letters* 11(12):2667-2670, 2009.

Yoo et al., "Highly Efficient Oxidative Amidation of Aldehydes with Amine Hydrrochloride Salts," *J. Am. Chem. Soc.* 128:13064-13065, 2006.

Zhang et al., "Electron-Rich, Bulky Ruthenium PNP-Type Complexes. Acceptorless Catalytic Alcohol Dehydrogenation," *Organometallics* 23:4026-4033, 2004.

Zhang et al., "Protein C-Terminal Modification through Thioacid/Azide Amidation," *Bioconjugate Chem.* 20:197-200, 2009.

Zhang et al., "Well-Defined N-Heterocyclic Carbene Based Ruthenium Catalysts for Direct Amide Synthesis from Alcohols and Amines," *Organometallics* 29:1374-1378, 2010.

Zweifel et al., "Catalyzed Dehydrogenative Coupling of Primary Alcohols with Water, Methonal, or Amines," *Angew. Chem. Int. Ed.* 48:559-563, 2009.

\* cited by examiner

40: $R^5 = R^6 = i\text{-Pr}$, X = Br
41: $R^5 = i\text{-Pr}$, $R^6 = $ Mes, X = I
42: $R^5 = R^6 = $ Me, X = I
43: $R^5 = R^6 = t\text{-Bu}$, X = Cl
44: $R^5 = R^6 = $ Mes, X = Cl 45
(prior art)

Ph⌒⌒OH + H₂N⌒Ph →[Ru catalyst, NHC precursor / L-type ligand, base, toluene, reflux] Ph⌒C(O)NH⌒Ph

| Entry | Catalyst | L-type Ligand | NHC precursor | Base | Time [h] | Yield[d] |
|---|---|---|---|---|---|---|
| 1[a] | RuCl₃ | pyridine | 40 | KO-t-Bu | 24 | 3% |
| 2[b] | [Ru(benzene)Cl₂]₂ | pyridine | 40 | KO-t-Bu | 24 | 54% |
| 3[b] | [Ru(benzene)Cl₂]₂ | PCy₃ | 40 | KO-t-Bu | 24 | 0% |
| 4[b] | [Ru(benzene)Cl₂]₂ | CH₃CN | 40 | KO-t-Bu | 24 | 55% |
| 5[b] | [Ru(p-cymene)Cl₂]₂ | pyridine | 40 | KO-t-Bu | 24 | 59% |
| 6[b] | [Ru(p-cymene)Cl₂]₂ | CH₃CN | 40 | KO-t-Bu | 24 | 58% |
| 7[b] | [Ru(benzene)Cl₂]₂ | CH₃CN | 41 | KO-t-Bu | 24 | 34% |
| 8[b] | [Ru(benzene)Cl₂]₂ | CH₃CN | 42 | KO-t-Bu | 24 | 19% |
| 9[b] | [Ru(benzene)Cl₂]₂ | CH₃CN | 44 | KO-t-Bu | 24 | 15% |
| 10[c] | [Ru(benzene)Cl₂]₂ | CH₃CN | 43 | NaH | 48 | 62% |
| 11[c] | [Ru(benzene)Cl₂]₂ | CH₃CN | 40 | NaH | 24 | 89% |
| 12[c] | [Ru(benzene)Cl₂]₂ | CH₃CN | 40 | NaH | 48 | 96% |
| 13[c] | [Ru(benzene)Cl₂]₂ | pyridine | 40 | NaH | 24 | 89% |
| 14[c] | [Ru(benzene)Cl₂]₂ | pyridine | 40 | NaH | 48 | 90% |
| 15[c] | [Ru(p-cymene)Cl₂]₂ | pyridine | 40 | NaH | 24 | 90% |
| 16[c] | [Ru(p-cymene)Cl₂]₂ | pyridine | 40 | NaH | 48 | 93% |
| 17[c] | [Ru(p-cymene)Cl₂]₂ | CH₃CN | 40 | NaH | 24 | 89% |
| 18[c] | [Ru(p-cymene)Cl₂]₂ | CH₃CN | 40 | NaH | 48 | 90% |
| 19[a] | RuCl₂(PPh₃)₃ | pyridine | 40 | NaH | 48 | 83% |
| 20[a] | RuCl₂(PPh₃)₃ | CH₃CN | 40 | NaH | 48 | 84% |
| 21[a] | RuCp*Cl₂ | pyridine | 40 | NaH | 24 | 16% |
| 22[a] | Ru(COD)Cl₂ | CH₃CN | 40 | NaH | 24 | 65% |
| 23[c] | [Ru(p-cymene)Cl₂]₂ | pyridine | none | NaH | 48 | 3% |
| 24[c] | [Ru(benzene)Cl₂]₂ | CH₃CN | none | NaH | 48 | 7% |
| 25[c] | [Ru(p-cymene)Cl₂]₂ | none | 40 | NaH | 48 | 3% |
| 26[c] | [Ru(benzene)Cl₂]₂ | none | 40 | NaH | 48 | 20% |

Fig. 5

| Entry | Alcohol | Amine | Amide | Yield [%][a] A[b] | B[c] |
|---|---|---|---|---|---|
| 1 | Ph~~~OH | Ph-NH₂ | Ph-C(O)-NH-CH₂-Ph | 90 | 96 |
| 2 | Ph~~~OH | (CH₂)₄-NH₂ | Ph-C(O)-NH-(CH₂)₅ | 98 | 97 |
| 3 | Ph~~~OH | (CH₂)₃-NH₂ | Ph-C(O)-NH-(CH₂)₄ | 97 | 91 |
| 4 | (CH₂)₄-OH | (CH₂)₃-NH₂ | (CH₂)₄-C(O)-NH-(CH₂)₄ | 99 | 95 |
| 5 | (CH₂)₄-OH | Ph-NH₂ | (CH₂)₄-C(O)-NH-CH₂-Ph | 91 | 92 |
| 6 | (CH₂)₄-OH | sec-(CH₂)₄-NH₂ | (CH₂)₄-C(O)-NH-CH(CH₃)(CH₂)₄ | 45 | 60 |
| 7 | 2-methylbutan-1-ol | Ph-NH₂ | 2-methylbutanoyl-NH-CH₂Ph | 77 | 70 |
| 8 | neopentyl-OH | Ph-NH₂ | pivaloyl-NH-CH₂Ph | 19 | 19 |
| 9 | HO-(CH₂)₄-NH₂ | | 2-piperidinone | 92 | 94 |
| 10 | CH₂=CH-(CH₂)₃-OH | Ph-NH₂ | (CH₂)₄-C(O)-NH-CH₂Ph | 72 | 92 |
| 11 | Ph-CH₂-OH | HN-piperidine | Ph-C(O)-N(piperidine) | 64 | 80 |
| 12 | Ph~~~OH | HN-morpholine | Ph-CH₂-C(O)-N(morpholine) | 63 | 90 |
| 13 | Ph~~~OH | Ph-CH₂-NH-CH₃ | Ph-CH₂-C(O)-N(CH₃)-CH₂-Ph | 58[d] | 69[d] |

(cont. on next page)

| Entry | Alcohol | Amine | Amide | Yield [%][a] A[b] | B[c] |
|---|---|---|---|---|---|
| 14 | Ph~~~OH | Ph\N/Ph (H) | Ph\C(=O)N(CH2Ph)(CH2Ph) | 0[d] | 0[d] |
| 15 | Ph~~~OH | H2N–Ph | Ph\C(=O)NH–Ph | 19[d] | 25[d] |
| 16 | Ph~~~OH | Ph\NH2 | Ph\C(=O)NH\CH2Ph | 55[e] | 23[e] |
| 17 | Ph–OH | Ph\NH2 | Ph\C(=O)NH\CH2Ph | 78 | 93 |

Fig. 5 (cont. from prev. page)

[Ru] = (NHC)L$_n$Ru

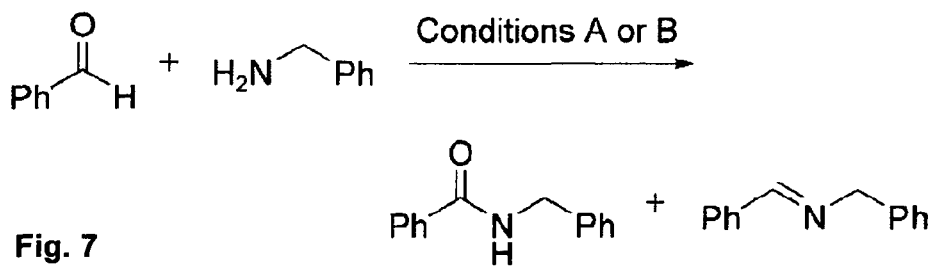
Fig. 7
| Entry | Conditions | Amide [%][a] | Imine [%][a] |
|---|---|---|---|
| 1 | A: ([Ru(p-cymene)Cl₂]₂) | 48 | 14 |
| 2 | B: ([Ru(benzene)Cl₂]₂) | 22 | 60 |
Fig. 8
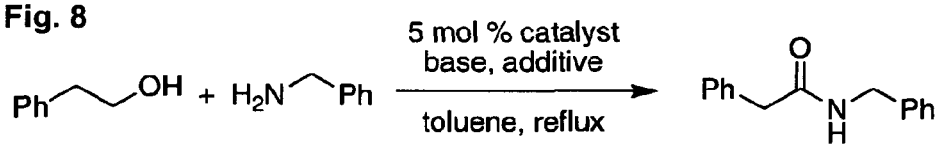
| entry | Ru complex | base | mol % | additive | mol % | yield[a] (%) |
|---|---|---|---|---|---|---|
| 1 | 48 | | | | | 0 |
| 2 | 48 | KO{^t}Bu | 5 | | | 7 |
| 3 | 48 | KO{^t}Bu | 10 | | | 82 |
| 4 | 48 | KO{^t}Bu | 15 | | | 93 |
| 5 | 49 | KO{^t}Bu | 15 | | | 93 |
| 6 | 48 | KO{^t}Bu | 20 | | | 89 |
| 7 | 48 | KO{^t}Bu | 40 | | | 60 |
| 8 | 48 | KO{^t}Bu | 60 | | | 50 |
| 9 | 48 | KO{^t}Bu | 100 | | | 10 |
| 10 | 48 | NaH | 20 | | | 93 |
| 11 | 48 | K₂CO₃ | 20 | | | 0 |
| 12 | 46 | KO{^t}Bu | 15 | | | 97 |
| 13 | 47 | KO{^t}Bu | 15 | | | 89 |
| 14 | 50 | KO{^t}Bu | 15 | | | 72 |
| 15 | 46 | KO{^t}Bu | 20 | | | 46[b] |
| 16 | 46 | KO{^t}Bu | 20 | NaBr | 100 | 44[b] |
| 17 | 46 | KO{^t}Bu | 20 | NaI | 100 | 42[b] |
| 18 | 46 | KO{^t}Bu | 20 | KBr | 100 | 46[b] |

Fig. 9

| entry | alcohol | amine | amide | yield[b] (%) |
|---|---|---|---|---|
| 1 | Ph⁓OH | Ph⁓NH₂ | Ph⁓C(O)NH⁓Ph | 93 |
| 2 | ⁓₄OH 10 | ⁓₃NH₂ 19 | ⁓₄C(O)NH⁓₄ 24 | 95 |
| 3 | ⁓₄OH | ⁓₄NH₂ 20 | ⁓₄C(O)NH-CH(CH₃)⁓₄ 25 | 56[c] |
| 4 | 2-methylbutan-1-ol 11 | Ph⁓NH₂ | CH₃CH₂CH(CH₃)C(O)NH⁓Ph 26 | 70 |
| 5 | PhCH₂OH 12 | piperidine 21 | PhC(O)-N(piperidine) 27 | 83 |
| 6 | Ph⁓OH | morpholine 22 | Ph⁓C(O)-N(morpholine) 28 | 65[c] |
| 7 | HO⁓NH₂ 13 | | 2-pyrrolidinone 29 | 68 |
| 8 | HO⁓⁓NH₂ 14 | | δ-valerolactam 30 | 88 |
| 9 | HO⁓⁓⁓NH₂ 15 | | ε-caprolactam 31 | 53 |
| 10 | 4-MeO-C₆H₄-CH₂OH 16 | Ph⁓NH₂ | 4-MeO-C₆H₄-C(O)NH-CH₂Ph 32 | 85 |

(cont. on next page)

| entry | alcohol | amine | amide | yield[b] (%) |
|---|---|---|---|---|
| 11 | Ph⌒OH | Ph⌒NH₂ | Ph-C(O)-NH-CH₂-Ph 33 | 81 |
| 12 | 4-F-C₆H₄-CH₂OH 17 | Ph⌒NH₂ | 4-F-C₆H₄-C(O)-NH-CH₂-Ph 34 | 66 |
| 13 | tBu-CH₂-OH 18 | Ph⌒NH₂ | tBu-C(O)-NH-CH₂-Ph 35 | 10 |
| 14 | Ph⌒⌒OH | H₂N—Ph 23 | Ph-CH₂-C(O)-NH-Ph 36 | 34[d] |

Fig. 9 (cont. from prev. page)

PROCESS OF FORMING AN AMIDE

CROSS REFERENCE TO RELATED APPLICATIONS

This application makes reference to and claims the benefit of priority of a provisional application for a "Ruthenium Catalysts for Direct Amide Synthesis from Alcohols and Amines" filed on Sep. 18, 2009 with the United States Patent and Trademark Office, and there duly assigned Ser. No. 61/243,803. The content of said application filed on Sep. 18, 2009 is incorporated herein by reference for all purposes, including an incorporation of any element or part of the description, claims or drawings not contained herein and referred to in Rule 20.5(a) of the PCT, pursuant to Rule 4.18 of the PCT.

FIELD OF THE INVENTION

The present invention relates to a process of forming an amide. In the process a primary or a secondary amine and a primary alcohol are contacted in the presence of Ruthenium (II) catalyst.

BACKGROUND OF THE INVENTION

The amide bond is a key functional group in organic chemistry. It plays a major role in the elaboration and composition of biological and chemical systems. Amides are typically synthesized by coupling of activated carboxylic acid derivatives with amines. Alternative strategies toward the synthesis of amides are the Staudinger reaction [Saxon, E, & Bertozzi, C R, *Science* (2000) 287, 2007; Damkaci, F, & DeShong, P, *J. Am. Chem. Soc.* (2003) 125, 4408; Gololobov, Y G, & Kasukhin, L F, Tetrahedron (1992) 48, 1353; Pianowski, Z, et al., *J. Am. Chem. Soc.* (2009) 131, 6492], the Schmidt reaction [Ribelin, T, et al., *Angew. Chem. Int. Ed.* (2008) 47, 6233; Lang, S, & Murphy, J A, *Chem. Soc. Rev.* (2006) 35, 146], Beckmann rearrangement [Owston, N A, et al., *Org. Lett.* (2007) 9, 3599; Hashimoto, M, et al., *J. Org. Chem.* (2008) 73, 2894], aminocarbonylation of haloarenes [Martinelli, J R, et al., *Angew. Chem. Int. Ed.* (2007) 46, 8460; Nanayakkara, P & Alper, H, *Chem. Commun.* (2003) 2384], alkenes [Beller, M, et al., *J. Mol. Catal. A: Chem.* (1995) 104, 17] and alkynes [Ali, B E, & Tijani, J, *Appl. Organomet. Chem.* (2003) 17, 921; Knapton, D J, & Meyer, T Y, *Org. Lett.* (2004) 6, 687; Uenoyama, Y, et al., *Angew Chem. Int. Ed.* (2005) 44, 1075; Park, J H, et al., *Org. Lett.* (2007) 9, 2465], oxidative amidation of aldehydes [Chang, J W W, & Chan, P W H, *Angew Chem. Int. Ed.* (2008) 47, 1138; Yoo, W J, & Li, C J, *J. Am. Chem. Soc.* (2006) 128, 13064; Tillack, A, et al., *Eur. J. Org. Chem.* (2001) 523; Naota, T, & Murahashi, S-I, *Synlett* (1991) 693], hydrative amide synthesis with alkynes [Cho, S, et al., *J. Am. Chem. Soc.* (2005) 127, 16046] and the amidation of thioacids with azides [Kolakowski, R V, et al., *J. Am. Chem. Soc.* (2006) 128, 5695; Zhang, X, et al., *Bioconjugate Chem.* (2009) 20, 197]. However, most of these methods require equimolar amounts of various reagents and generate tantamount of byproducts as waste with tedious procedures. Therefore, synthesis of amides under neutral conditions and without the generation of waste is a challenging goal.

Recently, the Milstein group reported an environmentally friendly direct amidation of alcohols and amines with liberating two molecules of hydrogen using a ruthenium PNN pincer, complex without any base or acid promoters [US patent application 2009/0112005; Gunanathan, C, et al., *Science* (2007) 317, 790]. This Milstein catalyst has been commercialized through Strem Chemicals, Inc (Newburyport, Mass.). Since then, several groups have reported the amide synthesis from alcohols and amines using ruthenium [Watson, A J A, et al, *Org. Lett.* (2009) 11, 2667; Nordstrøm, L U, et al., *J. Am. Chem. Soc.* (2008) 130, 17672] and rhodium [Zweifel, T, et al., *Angew. Chem. Int. Ed.* (2009) 48, 559] catalysts. Particularly, the Madsen group showed that $Ru(COD)Cl_2$ with an N-heterocyclic carbene (NHC) and phosphine ligands also catalyzed the formation of an amide rather than the alkylation of an amine. The direct acylation of amines with alcohols is a highly atom economical transformation with hydrogen as a sole byproduct and less waste than traditional amide synthesis. A drawback of such methods of amide production using phosphines is the high toxicity of these compounds, a concentration of 2.8 mg phosphine per liter air being lethal. Further, tertiary phosphines are often air sensitive and are subject to P—C bond degradation at elevated temperatures. In addition, phosphines are expensive. Hence, there remains a need for a further process of forming amides.

It is accordingly an object of the present invention to provide a process that is suitable for the production of amides and that avoids at least some of the above named draw-backs in current processes of amide production. This object is solved by the method of claim 1.

SUMMARY OF THE INVENTION

The present invention provides a process that involves subjecting an amino group and a hydroxyl (alcohol) group to an intramolecular and/or intermolecular oxidative coupling reaction, whereby an amide is formed. The process involves the use of a Ruthenium (II) catalyst, which may be formed from a Ruthenium (II) precatalyst complex. The use of this Ruthenium (II) catalyst involves providing an N-heterocyclic carbene, which may define a ligand of the Ruthenium (II) catalyst.

Accordingly, the invention provides a process of forming an amide. The process includes providing a primary or a secondary amine. The process also includes providing a primary alcohol. The primary or secondary amine and the primary alcohol are either (i) a primary or secondary amine moiety of a first reactant and a primary alcohol moiety of a second reactant, or they are (ii) two moieties of the same compound, namely a first moiety and a second moiety of the same compound. A respective first moiety is a primary or secondary amine, and a respective second moiety is a primary alcohol. The process further includes providing a Ruthenium (II) catalyst. The Ruthenium (II) catalyst is free of a phosphine ligand. Providing the Ruthenium (II) catalyst includes providing an N-heterocyclic carbene. The process also includes contacting the primary or secondary amine and the primary alcohol in the presence of the Ruthenium (II) catalyst. The process is carried out in the absence of a phosphine.

In some embodiments providing the Ruthenium (II) catalyst may involve the formation of one or more Ruthenium (II) complexes of formulae (IV), (V) and (VI)

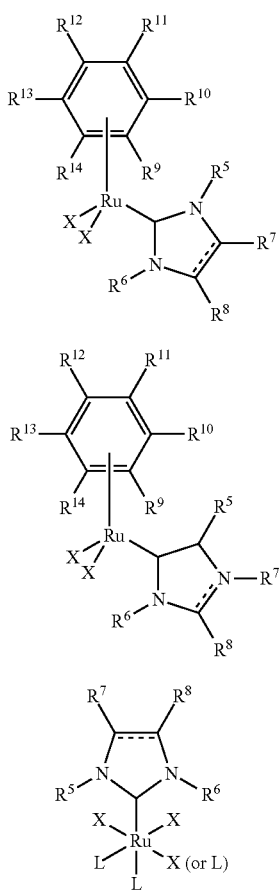

In these formulae the symbol ⚌ indicates that the respective bond may be a single or a double bond. $R^5$-$R^{14}$ are independently from one another selected from H, an aliphatic group, an alicyclic group, an aromatic group, an arylaliphatic group, and an arylalicyclic group. The aliphatic, alicyclic, aromatic, arylaliphatic or arylalicyclic group includes 0 to about 3 heteroatoms. Such a heteroatom may be selected from N, O, S, Se and Si. In the above formulae (IV)-(VI) X is halogen or —$OR^{15}$. $R^{15}$ in this moiety —$OR^{15}$ is one of H, an aliphatic group, an alicyclic group, an aromatic group, an arylaliphatic group, and an arylalicyclic group. The aliphatic, alicyclic, aromatic, arylaliphatic or arylalicyclic group includes 0 to about 3 heteroatoms. Such a heteroatom may be selected from N, O, S, Se and Si. In the above formulae (IV)-(VI) L is a solvent molecule, pyridine, acetonitrile or an N-heterocyclic carbene.

BRIEF DESCRIPTION OF THE DRAWINGS

The invention will be better understood with reference to the detailed description when considered in conjunction with the non-limiting examples and the accompanying drawings.

FIG. 4 shows examples of a reaction of the primary amine benzylamine and the primary alcohol 2-phenylethanol in the presence of a Ruthenium (II) catalyst according to the invention ([a]: 5 mol % Ru catalyst, 5 mol % NHC precursor (cf. FIG. 2), 5 mol % L-type ligand, 15 mol % base; [b]: 5 mol % Ru catalyst, 10 mol % NHC precursor, 10 mol % L-type ligand, 30 mol % base; [c]: 2.5 mol % Ru catalyst, 5 mol % NHC precursor, 5 mol % L-type ligand, 15 mol % base; [d]: determined by GC).

FIG. 5 depicts examples of a reaction of a primary or secondary amine and a primary alcohol in the presence of a Ruthenium (II) catalyst according to the invention ([a]: Isolated yields; [b]: Conditions A: [Ru(p-cymene)Cl$_2$]$_2$ (2.5 mol %), NHC precursor 1 (see FIG. 2, 5 mol %), NaH (15 mol %), and pyridine (5 mol %) in toluene at reflux for 36 h.; [c]: Conditions B: [Ru(benzene)Cl$_2$]$_2$ (2.5 mol %), NHC precursor 1 (see FIG. 2, 5 mol %), NaH (15 mol %), acetonitrile (5 mol %) in toluene for 36 h; [d]: in mesitylene at 163° C. for 36 h.; [e]: 1 mol % catalyst loading, GC yields.

FIG. 7 depicts data of the reaction between benzaldehyde and benzylamine under conditions A and B (see above; [a]: GC yields).

FIG. 8 illustrates the optimization of conditions using Ruthenium (II) complexes depicted in FIG. 3. Conditions used were 5 mol % catalyst, toluene, reflux, 24 h, unless otherwise noted (a: Determined by GC using dodecane as an internal standard; b: 80° C., 24 h).

FIG. 9 depicts the direct amide synthesis catalyzed by complex 46 (see FIG. 3); a: Catalyst 46 (5 mol %); KOtBu (15 mol %), toluene, reflux, 24 h, unless otherwise noted; b: isolated yields, average of two runs; c: 20 mol % KOtBu; d: mesitylene, 163° C.

DETAILED DESCRIPTION OF THE INVENTION

Figure 1A:
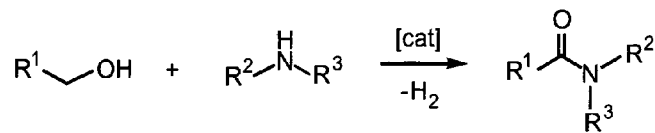
FIG. 1 illustrates a reaction in a process according to the present invention, using two reactants (A) or an intramolecular reaction between an amine and a hydroxyl moiety (B).

As noted above, previous catalyst systems of amide formation by direct amidation of alcohols and amines are environmentally friendly, but all such systems are based on phosphine ligands. The process of the present invention is based on the use of a phosphine-free catalyst system.

The terms "catalyst" and "catalyst system" are used interchangeably herein. As used herein, these terms refer to a compound or component, or combination of compounds or components that that is/are capable of increasing the rate of a chemical reaction. Thereby the catalyst or catalyst system generally facilitate(s) or allow(s) the reaction between one or more other compounds, the catalyst remaining in or returning to its original state. A catalyst may be used in any desired amount relative to the other components whose reactions is facilitated or allowed.

In a process of the present invention a Ruthenium (II) catalyst is provided. Providing the Ruthenium (II) catalyst in a process according to the invention includes providing an N-heterocyclic carbene. As an example, a Ruthenium (II)

precatalyst catalyst complex may be provided and an N-heterocyclic carbene, for example together, at the same time or in sequence, e.g. in a preselected order. In some embodiments the N-heterocyclic carbene may provided as a complex with a metal halogenide or metal oxide, such as a transition metal halogenide or a transition metal oxide, e.g. a halogenide or oxide of a metal of one of groups 3 to 12 of the periodic table of elements, including group 8, group 9, group 10 or group 11 thereof. An illustrative example of a group 11 halogenide is a silver halogenide, e.g. Ag(I)Cl, Ag(I)Br or Ag(I)I. An illustrative example of a group 11 oxide is copper (II) oxide, CuO.

An N-heterocyclic carbene is known in the art via the understanding of a molecule with a divalent carbon atom that has six valence electrons. While carbenes in general are typically very short lived, an N-heterocyclic carbene is stable as a ligand, generally a two electron ligand. An N-heterocyclic carbene can be understood as being stabilized by the electron lone pair(s) of one or more nitrogen atoms in the molecule, which can contribute to a resonance effect, which can be depicted in the form of mesomer structures, and be taken to lead to a partial multiple bond character of the additional electrons of the carbene moiety. An N-hetero-cyclic carbene generally has to be handled under inert gas atmosphere such as argon or nitrogen, prevented from contact with chlorinated solvents and moisture and is then stable even at elevated temperatures such as 200° C. and higher. A brief overview on stable carbenes including N-heterocyclic carbenes has been given by Kirmse (Angew. Chem. Int. Ed (2004) 43, 1767-1769). The formation, reactivity and theoretical aspects of N-heterocyclic carbenes have for example been reviewed by Hahn & Jahnke (Angew. Chem. Int. Ed (2008) 47, 3122-3172).

Examples of an N-heterocyclic carbene that is frequently used in the art and that may also be used in the context of the present invention include, but is not limited to one of the following molecules:

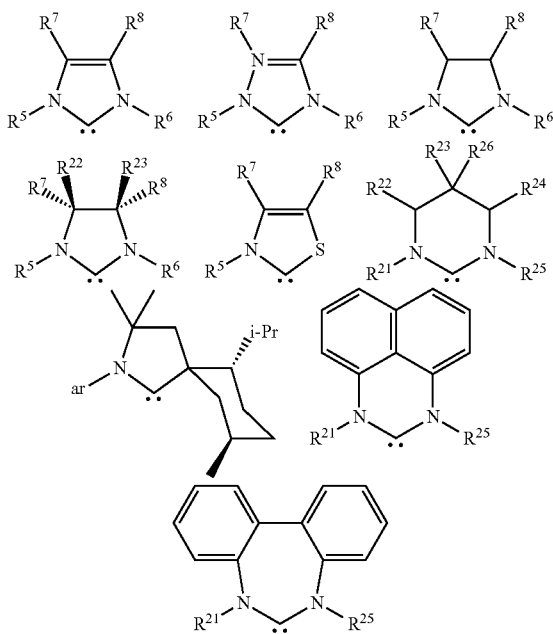

On a general basis an N-heterocyclic carbene can be formed from the corresponding proton-substituted compound using a strong base, i.e. a base such as a metal hydride, e.g. NaH, CaH$_2$, LiH or TiH$_2$. Further examples of a strong base include, but are not limited to, lithium diisopropylamide, lithium tetramethylpiperidide or lithium hexamethyldisilazide, each of them having a pK$_a$ of 30 or more in DMSO. In some embodiments an alkoxide can also be used as the respective base, such as NaOCH$_3$, KOtBu, NaOEt. Yet further examples of a suitable base are Li[N(SiMe$_3$)$_2$] and K[N(SiMe$_3$)$_2$]. In some embodiments at least one equivalent of the base, at least two or at least three equivalents of the base or more, is/are used relative to the proton-substituted compound (e.g. imidazole or imidazoline compound), typically being an N-heterocyclic compound.

In some embodiments the nitrogen atom(s) of the N-heterocyclic carbene is/are included in a 5-membered ring such as an imidazol-based, a triazol-based, a thiazol-based or a benzimidazol-based carbene. An imidazol-based carbene can for example be prepared from an imidazolium salt using a base or by reductive desulfurization of an imidazolin-2-thion (see e.g. chapter 2.3 of Hahn et al., 2008, supra). The respective imidazolium salt can for example be obtained via a cyclisation reaction or by a reaction at an N atom of an imidazol compound, such as alkylation, as summarized by Hahn et al. (ibid.). Imidazol-based N-heterocyclic carbenes have also been reviewed by Kühl (Chem Soc Rev (2007) 36, 592-607).

In the above examples of an N-heterocyclic carbene the moieties $R^5$, $R^6$, $R^7$ and $R^8$, where present, may independent from one another be H or an aliphatic, an alicyclic, an aromatic, an arylaliphatic, or an arylalicyclic group, which may include 0 to about 3 heteroatoms. Any two of these moieties, where present, such as $R^7$ and $R^8$, $R^5$ and $R^7$ or $R^6$ and $R^8$ may also be linked to define a bridge, such as an aliphatic, an aromatic, an alicyclic or an arylalicyclic bridge. "ar" in the fourth exemplary compound depicted above represents an aromatic moiety. $R^{21}$, $R^{22}$, $R^{23}$, $R^{24}$, $R^{25}$ and $R^{26}$, where present, may also independent from one another, be H or an aliphatic, an alicyclic, an aromatic, an arylaliphatic, or an arylalicyclic group, which may include 0 to about 3 hetero atoms.

A respective aliphatic, alicyclic, aromatic, arylaliphatic or arylalicyclic group of any of $R^5$, $R^6$, $R^7$, $R^8$, $R^{21}$, $R^{22}$, $R^{23}$, $R^{24}$, $R^{25}$ and $R^{26}$, where present, is typically of a main chain length of 1 to about 10, to about 15 or to about 20 carbon atoms. Each of $R^5$, $R^6$, $R^7$, $R^8$, $R^{21}$, $R^{22}$, $R^{23}$, $R^{24}$, $R^{25}$ and $R^{26}$, (as well as $R^9$, $R^{10}$, $R^{11}$, $R^{12}$, $R^{13}$ and $R^{14}$, and $R^1$, $R^2$ and $R^3$, see below) may for example include 0 to about 3, such as one or two, heteroatoms selected from the group N, O, S, Se and Si. Any of these aliphatic, alicyclic, aromatic, arylaliphatic or arylalicyclic groups may be substituted (see also below), for example carrying a silyl group, which may be of the structure:

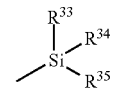

In such a silyl group moieties $R^{33}$-$R^{35}$ are independently selected aliphatic, alicyclic, aromatic, arylaliphatic, or arylalicyclic groups, typically bonded to the Si-atom via a carbon atom (which is part of the respective group).

Any two of these moieties, where present, such as $R^{21}$ and $R^{22}$, $R^{24}$ and $R^{25}$, $R^{22}$ and $R^{23}$, $R^{22}$ and $R^{25}$ or $R^{25}$ and $R^{26}$ may and $R^{23}$, also be linked to define a bridge, such as an aliphatic, an aromatic, an alicyclic or an arylalicyclic bridge. As an illustrative example of a compound depicted above with two aromatic bridges may serve:

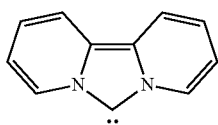

As a further illustrative example of a compound depicted above with an aromatic bridge, in which two carbene moieties are present, may serve:

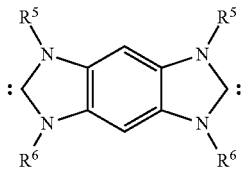

A further illustrative example of a compound depicted above with a bridge, in which two carbene moieties are present is a molecule with a moiety $R^6$ that includes an N-heterocyclic carbene moiety such as:

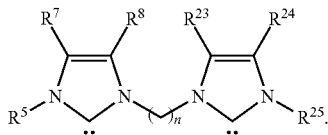

Moieties $R^{23}$ to $R^{25}$ in this example are as defined above, and n may be an integer selected from 1, 2, 3, 4 and 5.

As an illustrative example, the N-heterocyclic carbene may be imidazol- or imidazoline based and have the general formula:

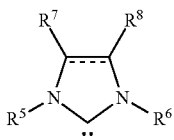

In this formula the symbol ⚌ indicates that the respective bond may be a single or a double bond. Accordingly, a corresponding N-heterocyclic carbene may also be represented by one of the two formulas

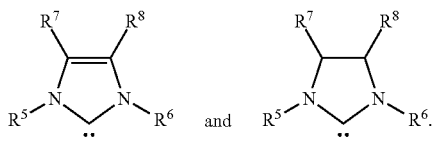

Such an N-heterocyclic carbene may be formed from an imidazole or an imidazoline compound and a base (supra). The imidazole compound may be of general formula (I), and the imidazoline compound may be of general formula (II):

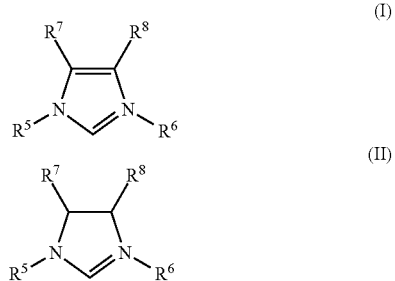

As explained above, $R^5$-$R^8$ are independently selected from H, an aliphatic group, an alicyclic group, an aromatic group, an arylaliphatic group, and an arylalicyclic group. A respective aliphatic, alicyclic, aromatic, arylaliphatic or arylalicyclic group may include 0 to about 3 heteroatoms selected from the group N, O, S, Se and Si.

The term "aliphatic" means, unless otherwise stated, a straight or branched hydro-carbon chain, which may be saturated or mono- or poly-unsaturated and include heteroatoms (see below). An unsaturated aliphatic group contains one or more double and/or triple bonds (alkenyl or alkynyl moieties). The branches of the hydrocarbon chain may include linear chains as well as non-aromatic cyclic elements. The respective hydrocarbon chain, which may, unless otherwise stated, be of any length, and contain any number of branches. Typically, the hydrocarbon (main) chain includes 1 to 5, to 10, to 15 or to 20 carbon atoms. Examples of alkenyl radicals are straight-chain or branched hydrocarbon radicals which contain one or more double bonds. Alkenyl radicals generally contain about two to about twenty carbon atoms and one or more, for instance two, double bonds, such as about two to about ten carbon atoms, and one double bond. Alkynyl radicals normally contain about two to about twenty carbon atoms and one or more, for example two, triple bonds, preferably such as two to ten carbon atoms, and one triple bond. Examples of alkynyl radicals are straight-chain or branched hydrocarbon radicals which contain one or more triple bonds. Examples of alkyl groups are methyl, ethyl, propyl, butyl, pentyl, hexyl, heptyl, octyl, nonyl, decyl, the n isomers of these radicals, isopropyl, isobutyl, isopentyl, sec-butyl, tert-butyl, neopentyl, 3,3 dimethylbutyl. Both the main chain as well as the branches may furthermore contain heteroatoms as for instance N, O, S, Se or Si, or carbon atoms may be replaced by these heteroatoms.

The term "alicyclic" may also be referred to as "cycloaliphatic" and means, unless otherwise stated, a non-aromatic cyclic moiety (e.g. hydrocarbon moiety), which may be saturated or mono- or poly-unsaturated. The cyclic hydrocarbon moiety may also include fused cyclic ring systems such as decalin and may also be substituted with non-aromatic cyclic as well as chain elements. The main chain of the cyclic hydrocarbon moiety may, unless otherwise stated, be of any length and contain any number of non-aromatic cyclic and chain elements. Typically, the hydrocarbon (main) chain includes 3, 4, 5, 6, 7 or 8 main chain atoms in one cycle. Examples of such moieties include, but are not limited to, cyclopentyl, cyclohexyl, cycloheptyl, or cyclooctyl. Both the cyclic hydrocarbon moiety and, if present, any cyclic and chain substituents may furthermore contain heteroatoms, as for instance N, O, S, Se or Si, or a carbon atom may be replaced by these heteroatoms. The term "alicyclic" also includes cycloalkenyl moieties that are unsaturated cyclic hydrocarbons, which generally contain about three to about eight ring carbon atoms, for example five or six ring carbon atoms. Cycloalkenyl radicals typically have a double bond in the respective ring system. Cycloalkenyl radicals may in turn be substituted.

The term "aromatic" means, unless otherwise stated, a planar cyclic hydrocarbon moiety of conjugated double bonds, which may be a single ring or include multiple fused or covalently linked rings, for example, 2, 3 or 4 fused rings. The term aromatic also includes alkylaryl. Typically, the hydrocarbon (main) chain includes 5, 6, 7 or 8 main chain atoms in one cycle. Examples of such moieties include, but are not limited to, cylcopentadienyl, phenyl, napthalenyl-, [10] annulenyl-(1,3,5,7,9-cyclodecapentaenyl-), [12] annulenyl-, [8] annulenyl-, phenalene (perinaphthene), 1,9-dihydropyrene, chrysene (1,2-benzophenanthrene). An example of an alkylaryl moiety is benzyl. The main chain of the cyclic hydrocarbon moiety may, unless otherwise stated, be of any length and contain any number of heteroatoms, as for instance N, O and S. Examples of such heteroaromatic moieties (which are known to the person skilled in the art) include, but are not limited to, furanyl-, thiophenyl-, naphtyl-, naphthofuranyl-, anthrathiophenyl-, pyridinyl-, pyrrolyl-, quinolinyl, naphthoquinolinyl-, quinoxalinyl-, indolyl-, benzindolyl-, imidazolyl-, oxazolyl-, oxoninyl-, oxepinyl-, benzoxepinyl-, azepinyl-, thiepinyl-, selenepinyl-, thioninyl-, azecinyl-(azacyclodecapentaenyl-), diazecinyl-, azacyclododeca -1,3,5,7,9,11-hexaene-5,9-diyl-, azozinyl-, diazocinyl-, benzazocinyl-, azecinyl-, azaundecinyl-, thia[11]annulenyl-, oxacyclotrideca-2,4,6,8,10,12-hexaenyl- or triazaanthracenyl-moieties.

By the term "arylaliphatic" is meant a hydrocarbon moiety, in which one or more aromatic moieties are substituted with one or more aliphatic groups. Thus the term "arylaliphatic" also includes hydrocarbon moieties, in which two or more aryl groups are connected via one or more aliphatic chain or chains of any length, for instance a methylene group. Typically, the hydrocarbon (main) chain includes 5, 6, 7 or 8 main chain atoms in each ring of the aromatic moiety. Examples of arylaliphatic moieties include, but are not limited to, 1-ethyl-naphthalene, 1,1'-methylenebis-benzene, 9-isopropylanthracene, 1,2,3-trimethyl-benzene, 4-phenyl-2-buten -1-ol, 7-chloro-3-(1-methylethyl)-quinoline, 3-heptyl-furan, 6-[2-(2,5-diethylphenyl)ethyl]-4-ethyl-quinazoline or, 7,8-dibutyl-5,6-diethyl-isoquinoline.

The term "arylalicyclic" means a hydrocarbon moiety in which an alicyclic moiety is substituted with one or more aromatic groups. Three illustrative example of an arylalicyclic moiety are "phenylcyclohexyl", "phenylcyclopentyl" or "naphthylcyclohexyl". In typical embodiments an arylalicyclic moiety has a main chain of more than about 10 carbon atoms. In some embodiments an arylalicyclic moiety has a main chain of up to about 30 carbon atoms, such as up to about 28, up to about 25, up to about 22, up to about 20, up to about 18 up or to about 14 carbon atoms.

Each of the terms "aliphatic", "alicyclic", "aromatic", "arylaliphatic" and "arylali-cyclic" as used herein is meant to include both substituted and unsubstituted forms of the respective moiety. Substituents may be any functional group, as for example, but not limited to, amino, amido, azido, carbonyl, carboxyl, cyano, isocyano, dithiane, halogen, hydroxyl, nitro, organometal, organoboron, seleno, silyl, silano, sulfonyl, thio, thiocyano, trifluoromethyl sulfonyl, p-toluenesulfonyl, bromobenzenesulfonyl, nitrobenzenesulfonyl, and methane-sulfonyl.

A heteroatom is any atom that differs from carbon. Examples include, but are not limited to N, O, P, S, and Se. Where several heteroatoms are present within a moiety of a reactant, a product or other compound of the process of the invention, they are independently selected.

Providing the Ruthenium (II) catalyst in a method according to the invention may include forming the Ruthenium (II) catalyst, for example forming the Ruthenium (II) catalyst in situ. The Ruthenium (II) catalyst may be formed from a Ruthenium (II) precatalyst complex, which may be provided. Forming the Ruthenium (II) catalyst from a Ruthenium (II) precatalyst complex may include allowing a reaction, such as complex formation with the N-heterocyclic carbene. In some embodiments the Ruthenium catalyst is formed in situ from the N-heterocyclic carbene and a $[Ru(A)Cl_2]_2$ precatalyst complex in the presence of the base (supra). Moiety A in formula $[Ru(A)Cl_2]_2$ may be an aromatic, an arylaliphatic or an arylalicyclic compound. In some embodiments A is or includes an aromatic moiety that is free of nitrogen as a heteroatom in the respective aromatic ring(s) of the moiety. In some embodiments the ring of the aromatic moiety consists only of carbon atoms. Any such aromatic ring may carry one or more substituents that may include one or more heteroatoms, e.g. 0-3 heteroatoms, such as O, N, Si, S or Se. In some embodiments the moiety A is a hydrocarbon moiety that does not include any heteroatom. In some embodiments the moiety A in formula $[Ru(A)Cl_2]_2$ is a benzene based moiety. The term "benzene based" refers to a moiety that has a an aromatic moiety, the aromatic moiety being a benzene ring, i.e. an aromatic six-membered ring without a heteroatom. This aromatic ring may carry substituents such as one or more aliphatic or alicyclic groups as well as one or more functional groups such as a hydroxyl group, a seleno group, a thiol group, a silyl group, a silano group, a sulfonyl group, a nitro group, a carboxy group, a halogen, an amino group, an amido group, a cyano group, an isocyano group or a thiocyano group (see also above for examples). The benzene ring may also be linked or fused to an aromatic, an arylaliphatic or an arylalicyclic group.

In some embodiments a benzene based moiety has a single aromatic moiety, the aromatic moiety being the benzene ring. In such embodiments the aromatic cycle may nevertheless carry substituents such as one or more aliphatic or alicyclic groups as well as one or more functional groups (supra).

In some embodiments the benzene based moiety is of the general formula (III):

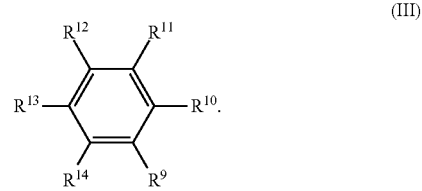

(III)

In formula (III) $R^9$-$R^{14}$ are independently selected from H, an aliphatic group, an alicyclic group, an aromatic group, an arylaliphatic group, and an arylalicyclic group. A respective aliphatic, alicyclic, aromatic, arylaliphatic or arylalicyclic group may include 0 to about 3 heteroatoms selected from the group N, O, S, Se and Si. As two illustrative examples, the benzene based moiety A in formula $[Ru(A)Cl_2]_2$ may be unsubstituted benzene or cymene.

In some embodiments providing the Ruthenium catalyst further includes providing a nitrogen containing ligand. In the art an atom or a molecule that is or that can be attached to a central atom, in the present case ruthenium (II), in a coordination or complex compound is called a ligand. Typically a ligands is capable of functioning as an electron-pair donor in a coordinate covalent bond (electron-pair bond) formed with the metal atom. Attachment of the ligand to the ruthenium atom may be through a single atom, e.g. the nitrogen atom, in which case can be called a unidentate ligand, or through two or more atoms, in which case it may be denoted a bidentate or polydentate ligand. In the field of organometallic chemistry, ligands are classified as "L-type", "X-type" and "Z-type". The classification by the symbols L, X, and Z, correspond respectively to 2-electron, 1-electron and 0-electron neutral ligands. X-type ligands are formed from an anionic precursor molecule and L-type ligands from a charge-neutral precursor molecule. Examples of L-type ligands are CO, a phosphine (e.g. $PPh_3$), a phosphite, an ether, a nitrile and an amine. In some embodiments a nitrogen containing ligand provided in a method of the invention is an L-type ligand, such as a nitrile and an amine, e.g. acetonitrile or pyridine.

In some embodiments, in particular if the ruthenium (II) catalyst is formed from a $[Ru(A)Cl_2]_2$ precatalyst complex (supra) and a metal halogenide complex of an N-hetero cyclic carbene, a nitrogen containing ligand such as an L-type ligand is not provided. The inventors have found that in such embodiments the formation of an amide proceeds smoothly in the absence of an additional nitrogen containing ligand such as an L-type ligand.

In some embodiments providing the Ruthenium (II) catalyst comprises forming one or more Ruthenium (II) complexes of formulae (IV), (V) and (VI)

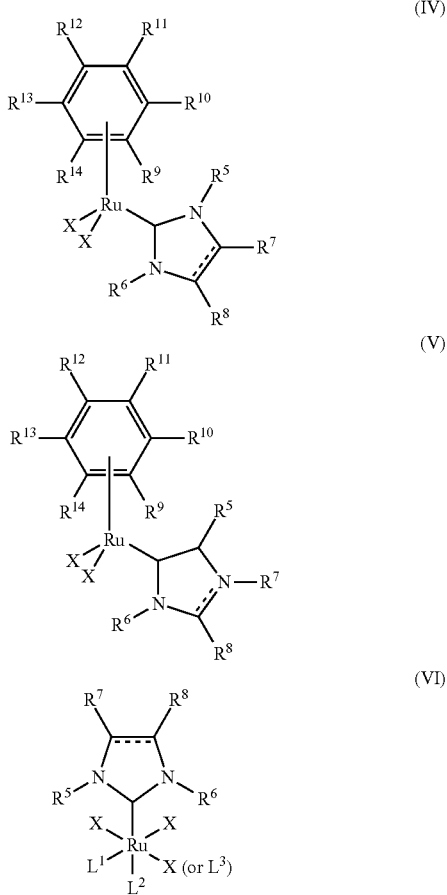

As defined above, $\rightleftharpoons$ represents a single or a double bond. $R^5$-$R^{14}$ are independently from one another H or an aliphatic, an alicyclic, an aromatic, an arylaliphatic or an arylalicyclic group. The respective aliphatic, alicyclic, aromatic, arylaliphatic or arylalicyclic group may have 0 to about 3, including 1 or 2, heteroatoms. Such a heteroatom may be N, O, S, Se or Si. X is halogen or —$OR^{15}$. $R^{15}$ in —$OR^{15}$ is H or an aliphatic, an alicyclic, an aromatic, an arylaliphatic or an arylalicyclic group. The respective aliphatic, alicyclic, aromatic, arylaliphatic or arylalicyclic group may have 0 to about 3, including 1 or 2, heteroatoms, such as N, O, S, Se or Si. $L^1$, $L^2$ and $L^3$ are independently selected from a solvent molecule, the L-type ligand (e.g. pyridine or acetonitrile, supra) and the N-heterocyclic carbene (supra). In some embodiments the Ruthenium catalyst that is provided can be represented by one of the above formulae (IV) to (VI).

Hence, in some embodiments a Ruthenium (II) catalyst of one or more of formulae (IV) to (VI) is provided, including formed, in a process according to the invention. In some embodiments a catalyst of one of formulae (IV) to (VI) is an intermediate that is formed in situ. In some embodiments a catalyst of one of formulae (IV) to (VI) is used in isolated, enriched or purified form. The term "isolated" means that a respective Ruthenium (II) catalyst is no longer included in a reaction mixture formed by adding e.g. a Ruthenium (II) precatalyst complex, such as a $[Ru(A)Cl_2]_2$ precatalyst complex, to a solvent, for instance together with an N-heterocyclic carbene. Rather, when isolated, the Ruthenium (II) catalyst has been removed from such solvent or solution, for instance the solution in which it was formed. The term "enriched" means that a respective Ruthenium (II) catalyst constitutes a significantly higher fraction of the total compounds, including the Ruthenium compounds, present in the matter, typically a solid or solution thereof, than in a reaction mixture in which the process of the invention has been carried out. Examples of enrichment are a filtration, a precipitation or a recrystallisation. The term "purified" means that a respective Ruthenium (II) catalyst constitutes a certain desired portion of the total matter, e.g. solid matter addressed. A purified Ruthenium (II) catalyst may for example be a solid matter, e.g. powder, which contains at least about 50%, about 60%, about 70%, about 80%, about 85%, about 90%, about 95% or more of Ruthenium (II) catalyst.

The Ruthenium (II) catalyst may in some embodiments be provided in catalytic amounts. Unless otherwise noted, the term "catalytic amount," as used herein, includes that amount of the Ruthenium (II) catalyst that is sufficient for a reaction of the process of the invention to occur. Accordingly, the quantity that constitutes a catalytic amount is any quantity that serves to allow or to increase the rate of reaction, with larger quantities typically providing a greater increase. The quantity used in any particular application will be determined to a large part by the individual needs of the manufacturing facility. Factors which enter into such a determination include the catalyst cost, recovery costs, desired reaction time, and system capacity. It will be most convenient to use an amount of Ruthenium (II) catalyst in the range from about 0.001 to about 0.5 equivalents, from about 0.001 to about 0.25 equivalents, from about 0.01 to about 0.25 equivalents, from about 0.001 to about 0.1, from about 0.01 to about 0.1 equivalents, including about 0.005, about 0.05 or about 0.08 equivalents of the primary or secondary amine, or in the range from about 0.001 to about 1 equivalents, from about 0.001 to about 0.5 equivalents, from about 0.001 to about 0.25 equivalents, from about 0.001 to about 0.1 equivalents, from about 0.01 to about 0.5 equivalents or from about 0.05 to about 0.1 equivalents, including about 0.015, about 0.02 or about 0.04 equivalents of the primary alcohol.

As noted above, a process according to the present invention is carried out without adding a phosphine. In particular the Ruthenium (II) catalyst used, including formed in the process of the invention, is free of a phosphine ligand. Typically the process is carried out in the absence of a phosphine.

After the ruthenium catalyst has been provided, a primary or a secondary amine and a primary alcohol are provided. The primary or secondary amine and the primary alcohol may be different molecules, i.e. reactants. In this case the (primary or secondary) amine and the (primary) alcohol are contacted in the presence of the Ruthenium (II) catalyst. The amine and the alcohol may also be different moieties of the same molecule. In this case the molecule that includes both the amine moiety and the alcohol moiety is exposed to the Ruthenium (II) catalyst. The primary alcohol may be of the general formula $R^1$—$CH_2$—OH, as also illustrated in FIG. 1A. In this formula $R^1$ may be an aliphatic, an alicyclic, an aromatic, an arylaliphatic or an arylalicyclic group (see also below). The respective aliphatic, alicyclic, aromatic, arylaliphatic or arylalicyclic group may have a main chain of a length of 1 to about 10, to about 15 or to about 20 carbon atoms. This aliphatic, alicyclic, aromatic, arylaliphatic or arylalicyclic group may include 0 to about 3, such as one or two, heteroatoms selected from N, O, S, Se and Si.

In some embodiments an aldehyde may be used instead of the primary alcohol. A respective aldehyde may be of the general formula $R^1$—CHO. In this formula $R^1$ is as defined above. In such an embodiment the invention also provides a process of forming an amide, as defined above. The process includes in such embodiments providing a primary or a secondary amine. The process also includes providing an aldehyde. The primary or secondary amine and the aldehyde are either (i) a primary or secondary amine moiety of a first reactant and an aldehyde moiety of a second reactant, or they are (ii) two moieties of the same compound, namely a first moiety and a second moiety of the same compound. A respective first moiety is a primary or secondary amine, and a respective second moiety is an aldehyde. The process in such an embodiment further includes providing a Ruthenium (II) catalyst as explained above. The process also includes contacting the primary or secondary amine and the aldehyde in the presence of the Ruthenium (II) catalyst. The process is in such an embodiment likewise carried out in the absence of a phosphine.

The primary or secondary amine may be of the general formula $R^2$—NH—$R^3$ (cf. also FIG. 1A). In this formula $R^2$ may be an aliphatic, an alicyclic, an aromatic, an arylaliphatic or an arylalicyclic group (see also below). Similar to $R^1$ the corresponding aliphatic, alicyclic, aromatic, arylaliphatic or arylalicyclic group may have a main chain of a length of 1 to about 10, to about 15 or to about 20 carbon atoms and include 0 to about 3, such as one or two, heteroatoms, e.g. N, O, S, Se or Si. $R^3$ is H or an aliphatic, an alicyclic, an aromatic, an arylaliphatic or an arylalicyclic group. Again, the respective aliphatic, alicyclic, aromatic, arylaliphatic or arylalicyclic group may have a main chain of a length of 1 to about 10, to about 15 or to about 20 carbon atoms and include 0 to about 3, such as one or two, heteroatoms selected from N, O, S, Se and Si.

As noted above, in some embodiments the amine and the primary alcohol, or the aldehyde, respectively, may be moieties of the same molecule. In an embodiment where an amino group and an alcohol group are included in the same molecule, the molecule may be represented by the general formula

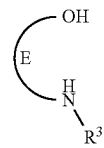

In an embodiment where an amino group and an aldehyde group are included in the same molecule, the molecule may be represented by the general formula

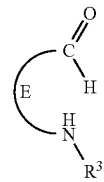

In these two formulae $R^3$ is as defined above. E in the two formulae above represents an aliphatic, an alicyclic, an aromatic, an arylaliphatic or an arylalicyclic bridge. This bridge may have a main chain of up to about 30 carbon atoms, such as 2 to about 25, including 2 to about 20, about 3 to about 20, about 4 to about 20, 2 to about 15, about 3 to about 15, about 4 to about 15, 2 to about 10, 2 to about 8, e.g. 3, 4, 5, 6, 7, 8, 9 or 10 carbon atoms. The aliphatic, alicyclic, aromatic, arylaliphatic or arylalicyclic bridge E may further include 0 to about 8, including 1, 2, 3, 4, 5, 6 or 7, heteroatoms, such as N, O, S, Se or Si.

Contacting the amine and the alcohol, or the amine and the aldehyde, respectively, in the presence of the catalyst, is typically carried out by adding the corresponding molecules into a suitable solvent. Likewise, the molecule that has the corresponding amine and alcohol moieties, or the corresponding amine and aldehyde moieties, respectively, is typically added into a suitable solvent. The term "contacting" the amine and the alcohol, or the amine and the aldehyde, respectively, as used herein encompasses providing a molecule that has an amine and an alcohol, or an amine and an aldehyde within the same molecule. By adding the corresponding molecule or molecules to the solvent a reaction mixture is formed. The reaction mixture may be brought to an elevated temperature, i.e. a temperature above ambient temperature. Ambient temperature is typically about 18° C. or about 20° C. The reaction mixture may for example be brought to a temperature above about 30° C., above about 40° C., above about 60° C., above about 80° C., above about 100° C., above about 120° C. or above about 140° C. The temperature may for example be selected in the range from about 25° C. to about 200° C., such as from about 30° C. to about 180° C., including about 40° C. to about 180° C., about 30° C. to about 110° C., about 40° C. to about 160° C., about 40° C. to about 110° C., about 50° C. to about 180° or about 60° C. to about 180° C. The temperature selected may for example be the boiling point of the reaction mixture, which is largely determined by the boiling point of the solvent used. As an illustrative example, if toluene is used as the solvent, the boiling point that may be selected as the temperature is about 120° C. As a further example, if mesitylene is used as the solvent, the boiling point is about 163° C.

Solvents used may be polar or non-polar liquids that are compatible with the ruthenium (II) catalyst complex used. Due to the sensitivity of the ruthenium (II) catalyst used, it may be disadvantageous to use a protic polar liquid and to use a chlorinated liquid (supra). Accordingly, typically a non-polar liquid is used that does not have a chlorine substituent. In addition the liquid used is in some embodiments free of substituents, which are capable of coordinating to ruthenium (II) due to the presence of electron lone pair(s). Hence, in some embodiments the liquid used as a solvent is free of substituents that have nitrogen, sulfur or oxygen atoms. Examples of non-polar liquids include, but are not limited to mineral oil, pentane, hexane, heptane, cyclohexane, cyclooctane, benzene, toluene, mesitylene, carbon disulfide, and a non-polar ionic liquid. Examples of a non-polar ionic liquid include, but are not limited to, 1-ethyl-3-methylimidazolium bis[(trifluoromethyl)sulfonyl]amide bis(triflyl)-amide, 1-ethyl-3-methylimidazolium bis[(trifluoromethyl)sulfonyl]amide trifluoroacetate, 1-butyl-3-methylimidazolium hexafluorophosphate, 1-hexyl-3-methylimidazolium bis(trifluoro-methylsulfonyl)imide, 1-butyl-3-methylimidazolium bis(trifluoromethylsulfonyl)imide, tri-hexyl(tetradecyl)phosphonium bis[oxalate (2-)]borate, 1-hexyl-3-methyl imidazolium tris-(pentafluoroethyl)trifluorophosphate, 1-butyl-3-methyl-imidazolium hexafluorophosphate, tris (pentafluoroethyl)trifluorophosphate, trihexyl (tetradecyl) phosphonium, N"-ethyl-N,N,N', N'-tetramethylguanidinium, 1-butyl-1-methylpyrroledinium tris(pentafluoroethyl)trifluoro-phosphate, 1-butyl-1-methylpyrrolidinium bis(trifluoromethylsulfonyl)imide, 1-butyl-3-methyl imidazolium hexafluorophosphate, 1-ethyl-3-methylimidazolium bis(trifluoromethyl-sulfonyl)imide and 1-n-butyl-3-methylimidazolium. In some embodiments the solvent used is an aromatic liquid that is free of halogen substituents. Illustrative examples of a respective aromatic liquid include, but are not limited to, benzene, toluene, mesitylene, p-xylene, m-xylene, ethylbenzene, propylbenzene, an ethyl toluene, p-cymene, o-cymene, cumene, naph-thalene, phenanthrene or pyrene.

Figure 1B:
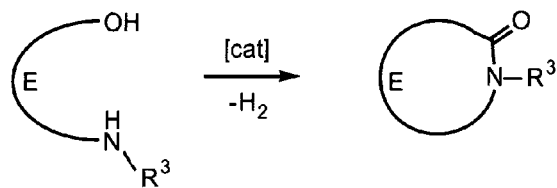

The reaction of forming an amide from an amine and an alcohol in a process of the invention; typically in the reaction mixture, can generally be represented by a reaction scheme as shown in FIG. 1A and FIG. 1B. FIG. 1A depicts an embodiment where the primary or secondary amine and the primary alcohol are defined by separate reactants. $R^1$ and $R^2$ are independently selected moieties, which may be an aliphatic, an alicyclic, an aromatic, an arylaliphatic or an arylalicyclic group. $R^3$ is H or an aliphatic, an alicyclic, an aromatic, an arylaliphatic or an arylalicyclic group. The respective aliphatic, alicyclic, aromatic, arylaliphatic or arylalicyclic group of $R^1$, $R^2$ and, where applicable, $R^3$, may have 0 to about 3, including 1 or 2, heteroatoms, such as N, O, S, Se or Si. [cat] represents the Ruthenium (II) catalyst provided in the process of the invention.

FIG. 1B depicts an embodiment where the primary or secondary amine and the primary alcohol are moieties of the same molecule. E represents an aliphatic, an alicyclic, an aromatic, an arylaliphatic or an arylalicyclic bridge, which may have a main chain of up to about 30 carbon atoms, such as 2 to about 25, including 2 to about 20, about 3 to about 20, about 4 to about 20, 2 to about 15, about 3 to about 15, about 4 to about 15, 2 to about 10, 2 to about 8, e.g. 3, 4, 5, 6, 7, 8, 9 or 10 carbon atoms (see also above). The bridge E may further include 0 to about 8, including 1, 2, 3, 4, 5, 6 or 7, heteroatoms, such as N, O, S, Se or Si. $R^3$ is as defined above.

In order that the invention may be readily understood and put into practical effect, particular, embodiments will now be described by way of the following non-limiting examples.

EXAMPLES

The following examples illustrate the use of catalyst systems using [Ru(p-cymene) Cl$_2$]$_2$ or [Ru (benzene)Cl$_2$]$_2$ complexes with an N-heterocyclic carbene and readily available nitrogen containing L-type ligands.

Figure 2:
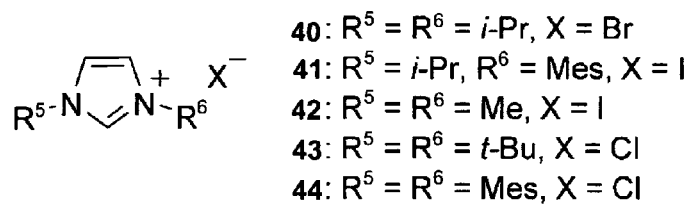
FIG. 2 depicts examples of precursors of N-heterocyclic carbenes.
Figure 3:
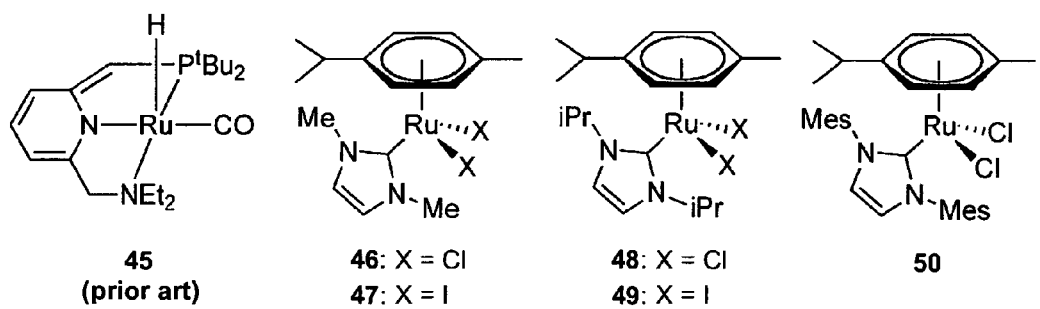
FIG. 3 depicts examples of Ruthenium (II) complexes suitable for an amide formation according to the invention.

A model reaction of 2-phenylethanol with benzyl-amine to afford N-benzyl-2-phenylacetamide was chosen (FIG. 3). In an initial attempt to generate the catalyst in situ using anhydrous RuCl$_3$, an L-type ligand, imidazolium salt 1 and potassium tert-butoxide as a base in refluxing toluene was unsuccessful (entry 1). Most of the starting materials remained unreacted and only 3% of the desired product was found on GC after 24 h. By changing the ruthenium precatalyst to [Ru(benzene)Cl$_2$]$_2$, the yield of amide was significantly increased to 54% with the help of a pyridine ligand (entry 2). Various L-type ligands such as acetonitrile, phosphines, and dimethyl fumarate were screened but only acetonitrile showed comparable activity with pyridine (entry 4). It is interesting to see economical and readily available nitrogen-containing pyridine and acetonitrile ligands working more efficiently than phosphines. The Madsen group reported that phosphines such as tricyclohexylphosphine (PCy$_3$) and tricyclopentylphosphine (PCyp$_3$) make Ru(COD)Cl$_2$ with N-heterocyclic carbene ligand active toward the amide synthesis (Nordstrøm, L U, et al., J. Am. Chem. Soc. (2008) 130, 17672). Among the NHC precursors examined (FIG. 2), 1 showed the best activity (entries 4 and 7-12).

A dramatic improvement of this catalytic system was achieved by changing the base from potassium tert-butoxide to sodium hydride (89%, entry 11). Running the reaction for an extended time, 48 h, did not result in a significant increase in conversion (entries 13-16). In the case of [Ru(p-cymene) Cl$_2$]$_2$, the pyridine ligand showed slightly better activity than acetonitrile (entries 15-18). On the other hand, in the case of [Ru(benzene)Cl$_2$]$_2$, acetonitrile showed a slightly better activity than pyridine (entries 11-14).

Other ruthenium complexes such as [RuCl$_2$(PPh$_3$)$_3$], RuCp*Cl$_2$, and Ru(COD)Cl$_2$ showed lower activity than [Ru (p-cymene)Cl$_2$]$_2$ and [Ru(benzene)Cl$_2$]$_2$ under the given conditions (entries 19-22). In the absence of the N-heterocyclic carbene ligand, the amide formation was very low with the observation of ~90% of starting materials and trace amounts of N-benzyl 2-phenylacetamide by alkylation of the amine (entries 23 and 24). A nitrogen-based L-type ligand is also essential for the facile formation of amide. Without pyridine or acetonitrile, it was also observed that most of the starting materials remained unreacted with 3-20% of N-benzyl 2-phenylacetamide formation (entries 25 and 26).

From the screening results, two sets of conditions were chosen to explore the scope and limitation of our methods— conditions A (2.5 mol % [Ru(p-cymene)Cl$_2$]$_2$, 5 mol % pyridine, 5 mol % NHC salt 1, and 15 mol % NaH) and conditions B (2.5 mol % [Ru(benzene)Cl$_2$]$_2$, 5 mol % acetonitrile, 5 mol % NHC salt 1, and 15 mol % NaH) in toluene at 120° C. The reaction time was further optimized and it was observed that there is no substantial increase of product after 24 h. However, a longer reaction time, 36 h, was chosen to completely consume the starting primary alcohols for the purpose of easier isolation. It was observed that ~5% of starting alcohol remains after 24 h and that it is all consumed after 36 h without substantial increase of amide formation. A period of 36 h was chosen as a reaction time for the facile purification of amides from trace amounts of remaining starting alcohols.

A range of amides were synthesized with good to excellent isolated yields under our systems (FIG. 4). Excellent yields of amides were obtained from the reaction of sterically unhindered alcohols and amines for both reaction conditions (entries 1-5). The amidation of 1-hexanol with 2-aminoheptane yielded 45% using [Ru(p-cymene)Cl$_2$]$_2$, while [Ru(benzene)Cl$_2$]$_2$ reached a better yield of 60% of the corresponding amide (entry 6). Reaction of 2-methylbutanol with benzylamine afforded 70-77% yield of corresponding amide (entry 7), while neopentyl alcohol with benzylamine gave just 19% yield of the corresponding amide (entry 8). These results indicate that the ruthenium-catalyzed direct amide formation is sensitive to steric hindrance as reported by others (Gunanathan, C, et al., Science (2007) 317, 790; Watson, A J A, et al., Org. Lett. (2009) 11, 2667; Nordstrøm, L U, et al., J. Am. Chem. Soc. (2008) 130, 17672). Intramolecular amidation was also carried out by using 5-aminopentanol with excellent yield (entry 9). The use of 5-hexen-1-ol gave the hexanamide with 100% reduction of double bond (entry 10) as observed by Madsen's group as well (Nordstrøm et al., 2008, supra).

In the case of cyclic secondary amines such as piperidine (entry 11) and morpholine (entry 12), [Ru(benzene)Cl$_2$]$_2$ (80%, piperidine, and 90%, morpholine) affords better yield than [Ru(p-cymene)Cl$_2$]$_2$ (64%, piperidine, and 63%, morpholine). The Williams group reported that [Ru(p-cymene)Cl$_2$]$_2$ and a bis(diphenylphosphino) butane-based catalytic system showed moderate catalytic activity in the morpholine case (Watson, et al., 2009, supra). The improved activity of our catalytic system is probably due to the more electron-donating N-heterocyclic carbene ligand system.

In the case of non-cyclic secondary amines such as N-benzylmethylamine, our system showed an improvement over Madsen's Ru(COD)Cl$_2$ catalytic system under the same conditions (entry 13, vs. 40% with Madsen's catalyst system, Nordstrøm et al., 2008, supra). However, with sterically hindered secondary amines such as dibenzylamine, the reaction did not proceed at all (entry 14). Also, the less basic aniline was less reactive even at 163° C. in mesitylene (entry 15). These limitation has also been observed with other ruthenium catalyst systems demonstrating challenges in this area (Gunanathan et al., 2007, supra; Watson et al., Nordstrøm et al., 2008, supra). Although catalytic systems according to the invention showed comparable or a slightly improved activity compared with Madsen's system under basic conditions, the turnover numbers (TONs) are less than those of the Milstein catalyst under neutral conditions (entry 16, vs. 960 TONs with Milstein's system). [Ru(p-cymene)Cl$_2$]$_2$ exhibited higher TONs than [Ru(benzene)Cl$_2$]$_2$ (55 vs. 23) presumably due to the better stability from the stronger p-coordination of p-cymene than benzene. Further investigations on electronic and steric effects of related ligands will be necessary to develop more improved catalytic systems.

It is assumed, without intend of being bound by theory, that the mechanism of the catalytic system used in the present invention is similar to that previously suggested. As further explained below, a suggested mechanism, depicted in FIG. 6, has been drafted on the basis of NMR data obtained with complex 46.

Interestingly, in contrast to the observation of Madsen's group, the inventors observed amide formation from benzaldehyde and benzylamine with the catalytic systems according to the invention with the concurrent formation of the imine (FIG. 7). However, lower conversions compared to the one from alcohol (48% from benzaldehyde vs. 78% from benzyl alcohol, conditions A, and 11% vs. 93%, conditions B, entry 17 in FIG. 4 and FIG. 7) suggest that Madsen group's postulation that the aldehyde generated from the alcohol stays coordinated to the metal is valid for the facile formation of an amide. The better conversion of benzaldehyde with more electron-rich [Ru(p-cymene)Cl$_2$]$_2$ also suggests that coordination to the aldehyde carbonyl is important to lead to amide formation. Various metal complexes have been reported for the oxidative amidation of aldehydes (Chang, J W W, & Chan, P W H., Angew. Chem. Int. Ed. (2008) 47, 1138; Yoo, W J, & Li, C J, J. Am. Chem. Soc. (2006) 128, 13064; Tillack, A., et al., Eur. J. Org. Chem. (2001) 523; Naota, T, & Murahashi, S I, Synlett (1991) 693).

Experimental Section
General Information

Unless otherwise noted, all reactions were carried out in oven-dried glassware under an inert atmosphere of dry argon or nitrogen. Reactions using compounds 45-50 (cf. FIG. 3) were carried out using standard Schlenk techniques or in an argon-filled glovebox. Dichloromethane, diethyl ether, and toluene were dried over a Pure Solv solvent purification system. 1,3-Dimethylimidazolium iodide (9) [Chu, Y, et al., J. Org. Chem. (2007) 72, 7790], (1,3-dimethylimidazol-2-ylidene)silver(I) iodide [Khramov, D M, et al., Organometallics (2007) 26, 6042], 1,3-diisopropylimidazolium bromide (5) [Starikova, O V, et al., J. Org. Chem. (2003) 39, 1467], and compound 50 [Lo, C, et al., Adv. Synth. Catal. (2007) 349, 546] were prepared by literature procedures. Other chemicals were purchased from commercial suppliers and used as received without further purification. All alcohols and amines were obtained from Aldrich or Alfa Aesar and used as received. Imidazolium salts 1-3 were synthesized by literature procedures (Starikova, O V, et al., Russ. J. Org. Chem. (2003) 39, 1467; Chu, Y, et al., J. Org. Chem. (2007) 72, 7790; Eguillor, B. et al., Organometallics (2008) 27, 445).

Analytical TLC was performed on a Merck 60 F254 silica gel plates (0.25 mm thickness). Column chromatography was performed on Merck 60 silica gel (230-400 mesh). Deuterated solvents were purchased from Cambridge Isotope Laboratories and dried over molecular sieves. NMR spectra were recorded in CDCl$_3$, CD$_2$Cl$_2$, or toluene-d$_8$ using a Bruker DPX300, AMX400, JEOL ECA400, or JEOL ECA400SL spectrometer. Tetramethysilane (TMS) was used as reference, and the chemical shifts were reported in ppm and the coupling constants in Hz. Elemental analyses were performed by the Elemental Analysis Laboratory of the Division of Chemistry and Biological Chemistry at Nanyang Technological University. GC yields were obtained on an Agilent 7890A instrument equipped with an HP-5 column using dodecane as an internal standard. Mass spectrometry was performed by Waters Q-T of Premier Micromass instrument, using the electro spray ionization (ESI) mode.

General Procedure for Amide Synthesis

[Ru(p-cymene)Cl$_2$]$_2$ (A, 15.3 mg, 0.025 mmol) or [Ru(benzene)Cl$_2$]$_2$ (B; 12.5 mg, 0.025 mmol), 1,3-diisopropylimidazolium bromide (11.7 mg, 0.05 mmol), NaH (3.6 mg, 0.15 mmol) and pyridine (A, 4 mL, 0.05 mmol) or acetonitrile (B, 2.6 mL, 0.05 mmol), were placed in an oven-dried Schlenk tube inside the glove box; toluene (0.6 mL) was added to the mixture there. The Schlenk tube was taken out and heated to reflux in an oil bath under an argon atmosphere. The flask was removed from the oil bath after 20 min and the alcohol (1 mmol) and the amine (1.1 mmol) were added. The mixture was heated to reflux under an argon atmosphere for 36 h. The reaction mixture was cooled to room temperature and the solvent was removed under vacuum and the residue was purified by silica gel flash column chromatography to afford the amide. All the amides were identified by spectral comparison with literature data or with analogous literature data.

N-Benzyl-2-phenylacetamide

Purified by silica gel column chromatography (hexane: ethyl acetate (EA) 3:1, $R_1$=0.26) to afford it as a white solid. Isolated yields; conditions A: 90%, conditions B: 96%.

$^1$H NMR (CDCl$_3$, 400 MHz): δ=7.39-7.26 (m, 10H), 5.70 (bs, 1H), 4.41 (d, 2H, J=5.9 Hz), 3.62 (s, 2H);

$^{13}$C NMR (CDCl$_3$, 100 MHz): δ=171.1, 138.3, 135.0, 129.6, 129.2, 128.8, 127.7, 127.6, 47.9, 43.7.

HR-MS (ESI): m/z=226.1236 [MH$^+$], calcd. for C$_{15}$H$_{16}$NO: 226.1232

N-Hexyl-2-phenylacetamide

Purified by silica gel column chromatography (hexane:EA 3:1, $R_f$=0.28) to afford a white solid. Isolated yields: conditions A: 98%, conditions B: 97%.

$^1$H NMR (CDCl$_3$, 400 MHz): δ=7.35-7.26 (m, 5 H), 5.47 (bs, 1H), 3.56 (s, 2 H), 3.19 (q, 2H, J=6.8 Hz), 1.43-1.37 (m, 2H), 1.29-1.17 (m, 6 H), 0.85 (t, J=6.8 Hz);

$^{13}$C NMR (CDCl$_3$, 100 MHz): δ=171.0, 135.2, 129.6, 129.2, 127.5, 44.0, 39.8, 31.5, 29.6, 26.7, 22.7, 14.1;

HR-MS (ESI): m/z=220.1698 [MH$^+$], calcd. for C$_{14}$H$_{22}$NO: 220.1701.

N-Pentyl-2-phenylacetamide

Purified by silica gel column chromatography (hexane:EA 3:1, $R_f$=0.28) to afford a white solid. Isolated yields: conditions A: 97%, conditions B: 91%.

$^1$H NMR (CDCl$_3$, 400 MHz): δ=7.37-7.24 (m, 5 H), 5.46 (bs, 1H), 3.56 (s, 2 H), 3.21-3.16 (m, 2 H), 1.41 (p, 2H, J=6.8 Hz), 1.30-1.17 (m, 4 H), 0.85 (t, 3H, J=7.2 Hz);

$^{13}$C NMR (CDCl$_3$, 100 MHz): δ=171.0, 135.2, 129.6, 129.2, 127.4, 44.0, 39.7, 29.3, 29.1, 22.4, 14.1;

HR-MS (ESI): m/z=206.1547 [MH$^+$], calcd. for C$_{13}$H$_{20}$NO: 206.1545.

N-Pentylhexanamide

Purified by silica gel column chromatography (hexane:EA 3:1, $R_f$=0.30) to afford a white solid. Isolated yields: conditions A: 99%, conditions B: 95%.

$^1$H NMR (CDCl$_3$, 400 MHz): δ=5.86 (bs, 1 H), 3.20-3.15 (m, 2H), 2.11 (t, 2H, J=7.7 Hz), 1.58 (p, 2H, J=8.2 Hz), 1.45 (p, 2H, J=7.2 Hz), 1.27-1.23 (m, 8 H), 0.86-0.82 (m, 6H);

$^{13}$C NMR (CDCl$_3$, 100 MHz): δ=173.4, 39.6, 36.9, 31.6, 29.5, 29.2, 25.7, 22.5, 22.4, 14.1, 14.0;

HR-MS (ESI): m/z=186.1852 [MH$^+$], calcd. for C$_{11}$H$_{24}$NO: 186.1858.

N-Benzylhexanamide

Purified by silica gel column chromatography (hexane:EA 3:1, $R_f$=0.28) to afford a white solid. Isolated yields: conditions A: 91%, conditions B: 92%.

$^1$H NMR (CDCl$_3$, 400 MHz): δ=7.30-7.26 (m, 5 H), 5.94 (bs, 1H), 4.41 (d, 2H, J=5.9 Hz), 2.19 (t, 2H, J=7.4 Hz), 1.66 (p, 2H, J=7.7 Hz), 1.32-1.28 (m, 4 H), 0.88 (t, 3H, J=6.8 Hz);

$^{13}$C NMR (CDCl$_3$, 100 MHz): δ=173.2, 138.6, 128.9, 128.0, 127.7, 43.7, 37.0, 31.7, 25.7, 22.6, 14.1;

HR-MS (ESI): m/z=206.1548 [MH$^+$], calcd. for C$_{13}$H$_{20}$NO: 206.1545.

N-(1-Methylhexyl)hexanamide

Purified by silica gel column chromatography (hexane:EA 3:1, $R_f$=0.30) to afford a colorless liquid. Isolated yields: conditions A: 45%, conditions B: 60%.

$^1$H NMR (CDCl$_3$, 400 MHz): δ=5.71 (d, 1H, J=7.7 Hz), 3.92-3.86 (m, 1 H), 2.08 (t, 2H, J=7.3 Hz), 1.55 (p, 2H, J=7.7 Hz), 1.39-1.15 (m, 12H), 1.04 (d, 3H, J=6.8 Hz), 0.84-0.80 (m, 6H);

$^{13}$C NMR (CDCl$_3$, 100 MHz): δ=172.6, 45.1, 37.0, 36.9, 31.8, 31.5, 25.8, 25.7, 22.7, 22.5, 21.1, 14.1, 14.0;

HR-MS (ESI): m/z=214.2169 [MH$^+$], calcd. for C$_{13}$H$_{28}$NO: 214.2171.

N-Benzyl-2-methylbutanamide

Purified by silica gel column chromatography (hexane:EA 3:1, $R_f$=0.26) to afford a white solid. Isolated yields: conditions A: 77%, conditions B: 70%.

$^1$H NMR (CDCl$_3$, 400 MHz): δ=7.30-7.25 (m, 5H), 6.19 (bs, 1 H), 4.45-4.37 (m, 2 H), 2.19-2.12 (m, 1 H), 1.73-1.62 (m, 1 H), 1.48-1.41 (m, 1 H), 1.15 (d, 3H, J=6.8 Hz), 0.91 (t, 3H, J=7.2 Hz);

$^{13}$C NMR (CDCl$_3$, 100 MHz): δ=176.6, 138.7, 128.7, 127.8, 127.4, 43.4, 43.2, 27.4, 17.7, 12.1;

HR-MS (ESI): m/z=192.1384 [MH$^+$], calcd. for C$_{12}$H$_{18}$NO: 192.1388.

N-Benzylpivalamide

Purified by silica gel column chromatography (hexane:EA 3:1, $R_f$=0.26) to afford a white solid. Isolated yields: conditions A: 19%, conditions B: 19%.

$^1$H NMR (CDCl$_3$, 400 MHz): δ=7.35-7.25 (m, 5 H), 5.93 (bs, 1H), 4.43 (d, 2H, J=5.9 Hz), 1.24 (s, 9H);

$^{13}$C NMR (CDCl$_3$, 100 MHz): δ=178.5, 138.8, 128.9, 127.8, 127.6, 43.8, 38.9, 27.8;

HR-MS (ESI): m/z=192.1390 [MH$^+$], calcd. for C$_{12}$H$_{18}$NO: 192.1388.

Piperidin-2-one

Purified by silica gel column chromatography (CH$_2$Cl$_2$: MeOH 19:1, $R_f$=0.30) to afford a white solid. Isolated yields: conditions A: 92%, conditions B: 94%.

$^1$H NMR (CDCl$_3$, 400 MHz): δ=7.52 (bs, 1 H), 3.19-3.16 (m, 2H), 2.21 (t, 2H, J=6.4 Hz), 1.72-1.60 (m, 4H);

$^{13}$C NMR (CDCl$_3$, 100 MHz): δ=172.9, 42.0, 31.4, 22.1, 20.8;

HR-MS (ESI): m/z=100.0761 [MH$^+$], calcd. for C$_5$H$_{10}$NO: 100.0762.

Phenyl(piperidin-1-yl)methanone

Purified by silica gel column chromatography (hexane:EA 3:1, $R_f$=0.31) to afford a sticky liquid. Isolated yields: conditions A: 64%, conditions B: 80%.

$^1$H NMR (CDCl$_3$, 400 MHz): δ=7.37 (bs, 5 H), 3.70 (bs, 2 H), 3.33 (bs, 2 H), 1.66-1.50 (m, 6H);

$^{13}$C NMR (CDCl$_3$, 100 MHz): δ=170.3, 136.5, 129.4, 128.4, 126.8, 48.8, 43.1, 26.6, 25.7, 24.6;

HR-MS (ESI): m/z=190.1232 [MH$^+$], calcd. for C$_{12}$H$_{16}$NO: 190.1232.

1-Morpholino-2-phenylethanone

Purified by silica gel column chromatography (hexane:EA 1:2, $R_f$=0.32) to afford a white solid. Isolated yields: conditions A: 63%, conditions B: 90%.

$^1$H NMR (CDCl$_3$, 400 MHz): δ=7.34-7.22 (m, 5H), 3.73 (s, 2 H), 3.63 (s, 4 H), 3.48-3.41 (m, 4H);

$^{13}$C NMR (CDCl$_3$, 100 MHz): δ=169.7, 134.9, 128.9, 128.6, 127.0, 66.8, 66.5, 46.6, 42.2, 40.9;

HR-MS (ESI): m/z=206.1182 [MH$^+$], calcd. for C$_{12}$H$_{16}$NO$_2$: 206.1181.

N-Benzylbenzamine

Purified by silica gel column chromatography (hexane:EA 2:1, $R_1$=0.29) to afford a white solid. Isolated yields: conditions A: 78%, conditions B: 93%.

$^1$H NMR (CDCl$_3$, 400 MHz): δ=7.80-7.78 (m, 2 H), 7.50-7.30 (m, 8 H), 6.48 (bs, 1 H), 4.64 (d, 2H, J=5.9 Hz);

$^{13}$C NMR (CDCl$_3$, 100 MHz): δ=167.5, 138.4, 134.5, 131.7, 128.9, 128.7, 128.0, 127.7, 127.2, 44.3;

HR-MS (ESI): m/z=212.1071 [MH$^+$], calcd. for C$_{14}$H$_{14}$NO: 212.1075.

N-Benzyl-N-methyl-2-phenylacetamide

Purified by silica gel column chromatography (hexane:EA 4:1, $R_f$=0.26) to afford a colorless liquid. Isolated yields: conditions A: 58%, conditions B: 69%. It contains 1:1.4 mixture of two rotamers.

HR-MS (ESI): m/z=240.1391 [MH$^+$], calcd. for C$_{16}$H$_{18}$NO: 240.1388.

Major rotamer: $^1$H NMR (CDCl$_3$, 400 MHz): δ=7.31-7.21 (m, 9H), 7.10-7.08 (m, 1H), 4.60 (s, 2H), 3.78 (s, 2H), 2.88 (s, 3H);

$^{13}$C NMR (CDCl$_3$, 100 MHz): δ=171.3, 137.3, 135.0, 129.0, 128.9, 128.6, 128.1, 126.9, 126.4, 51.0, 41.3, 35.3.

Minor rotamer: $^1$H NMR (CDCl$_3$, 400 MHz): δ=7.31-7.21 (m, 9H), 7.10-7.08 (m, 1H), 4.51 (s, 2H), 3.75 (s, 2H), 2.94 (s, 3H);

$^{13}$C NMR (CDCl$_3$, 100 MHz): δ=171.6, 136.5, 135.2, 129.0, 128.9, 128.8, 127.7, 127.4, 126.9, 53.7, 40.9, 34.1.

N,2-Diphenylacetamide

Purified by silica gel column chromatography (hexane:EA 4:1, Rf=0.31) to afford a white solid. Isolated yields: conditions A: 19%, conditions B: 25%.

$^1$H NMR (CDCl$_3$, 400 MHz): δ=7.42-7.24 (m, 10H), 7.12-7.05 (m, 1H), 3.71 (s, 2H);

$^{13}$C NMR (CDCl$_3$, 100 MHz): δ=169.4, 137.8, 134.6, 129.7, 129.4, 129.1, 127.8, 124.6, 120.0, 45.0;

HR-MS (ESI): m/z=212.1079 [MH$^+$], calcd. for C$_{14}$H$_{14}$NO: 212.1075.

The above results indicated that the NHC-based ruthenium complexes synthesized from [Ru(p-cymene)Cl$_2$]$_2$ such as 46 (Herrmann, W A, et al., J. Chem. Eur. J. (1996) 2, 772), 48, and 50 (Lo, C, et al., Adv. Synth. Catal. (2007) 349, 546) might be real catalytic intermediates for the direct amide synthesis (cf. FIG. 3). Identifying well-defined catalysts from in situ generated catalysts is important to investigate the mechanism and to further improve the activity by rational design of catalysts. Accordingly, the catalytic activity of the well-defined NHC-based ruthenium complexes was analyzed and the catalytic intermediates studied.

Synthesis of 46

A mixture of (1,3-dimethylimidazol-2-ylidene)silver(I) iodide (148.9 mg, 0.45 mmol) and [Ru(p-cymene)Cl$_2$]$_2$ (137.8 mg, 0.23 mmol) was stirred in CH$_2$Cl$_2$ at room temperature for 6 h. The white precipitate (AgI) was then filtered through Celite. After removal of the solvent under vacuum, analytically pure product 46 was obtained by washing the crude product with diethyl ether (3×5 mL). Yield: 93% (168.3 mg, 0.42 mmol).

$^1$H NMR (CD$_2$Cl$_2$, 400 MHz): δ 7.03 (s, 2H, CH$_{imid}$), 5.39 (d, J=5.96 Hz, 2H, CH$_{pcym}$), 5.06 (d, J=5.96 Hz, 2H, CH$_{pcym}$), 3.96 (s, 6H, NCH$_3$), 2.93 (septet, J=6.88 Hz, 1H, CH$_{isop\,pcym}$), 1.98 (s, 3H, CH$_{3pcym}$), 1.25 (d, J=6.84 Hz, 6H, CH$_{3isop\,pcym}$).

The formation of complex 46 was confirmed by comparing the chemical shifts of 1H NMR with reported values (Herrmann, W A, et al., Chem.; Eur. J. (1996) 2, 772).

Synthesis of 47

A Schlenk tube was charged with complex 46 (67.7 mg, 0.17 mmol), NaI (509.7 mg, 3.4 mmol), and 5 mL of THF. The reaction mixture was stirred at room temperature for 8 h. The solvent was removed under vacuum. The residue was dissolved in toluene, and the resulting suspension was passed through a plug of Celite. All the volatiles were removed, and the residue was washed with diethyl ether (3×5 mL) to give 47 as a dark red powder. Yield: 70% (69.8 mg, 0.12 mmol).

$^1$H NMR (CD$_2$Cl$_2$, 400 MHz): δ 7.08 (s, 2H, CH$_{imid}$), 5.59 (d, J=5.60 Hz, 2H, CH$_{pcym}$), 5.18 (d, J=5.56 Hz, 2H, CH$_{pcym}$), 4.04 (s, 6H, CH$_{3imid}$), 3.15 (septet, J=6.88 Hz, 1H, CH$_{isop\,pcym}$), 1.96 (s, 3H, CH$_{3pcym}$), 1.23 (d, J=6.88 Hz, 6H, CH$_{3isop\,pcym}$), $^{13}$C {$^1$H} NMR (CD$_2$Cl$_2$, 100 MHz): δ 170.4 (C-Ru), 124.4 (CH$_{imid}$), 110.0 (Cq$_{pcym}$), 99.9 (Cq$_{pcym}$), 86.6 (CH$_{pcym}$), 83.0 (CH$_{pcym}$), 44.9 (CH$_{3imid}$), 32.0 (CH$_{isop\,pcym}$), 23.0 (CH$_{3isop\,pcym}$); 19.2 (CH$_{3pcym}$).

Anal. calcd for C$_{16}$H$_{24}$Cl$_2$I$_2$N$_2$Ru (47 3CH$_2$Cl$_2$, 670.2): C, 28.68; H, 3.61; N, 4.18. Found: C, 28.41; H, 3.89; N, 4.33

Synthesis of 48

A suspension of 1,3-diisopropylimidazolium bromide (106.4 mg, 0.46 mmol) and Ag$_2$O (64.0 mg, 0.28 mmol) in CH$_2$Cl$_2$ was stirred at room temperature in the dark for 2 h. The mixture was then filtered through a plug of Celite, and to the filtrate was added [Ru(p-cymene)Cl$_2$]$_2$ (139.8 mg, 0.23 mmol).

The reaction mixture was stirred at room temperature for 2 h and then filtered through Celite. The solvent was removed under vacuum. Washing the crude product with diethyl ether (3×5 mL) can afford 48 as an orange powder. Yield: 90% (189.8 mg, 0.41 mmol).

$^1$H NMR (CD$_2$Cl$_2$, 300 MHz): δ 7.15 (s, 2H, CH$_{imid}$), 5.48 (d, J=5.97 Hz, 2H, CH$_{pcym}$), 5.34-5.25 (m, 2H, CH$_{isop\,pcym}$), 5.06 (d, J=6.00 Hz, 2H, CH$_{pcym}$), 2.94 (septet, J=6.96 Hz, 1H, CH$_{isop\,pcym}$), 2.01 (s, 3H, CH$_{3pcym}$), 1.42 (br, 12H, CH$_{3isop\,imid}$), 1.31 (d, J=6.93 Hz, 6H, CH$_{3isop\,pcym}$).

$^{13}$C {$^1$H} NMR (CD$_2$Cl$_2$, 100 MHz): δ 172.2 (C—Ru), 119.5 (CH$_{imid}$), 107.4 (Cq$_{pcym}$), 98.5 (Cq$_{pcym}$), 86.9 (CH$_{pcym}$), 82.0 (CH$_{pcym}$), 52.5 (CH$_{isop\,imid}$), 31.2 (CH$_{isop\,pcym}$), 25.5 (CH$_{3isop\,imid}$), 25.1 (CH$_{3isop\,imid}$), 22.9 (CH$_{3isop\,pcym}$), 19.2 (CH$_{3pcym}$).

Anal. calcd for C$_{20}$H$_{32}$Cl$_4$N$_2$Ru (48.3CH$_2$Cl$_2$, 543.4): C, 44.21; H, 5.94; N, 5.16. Found: C, 44.68; H, 5.63; N, 5.37.

Synthesis of 49

A Schlenk tube was charged with complex 3 (83.4 mg, 0.18 mmol), NaI (539.6 mg, 3.6 mmol), and 5 mL of THF. The reaction mixture was stirred at room temperature for 8 h. All volatiles were removed under vacuum. The residue was dissolved in toluene, and the resulting suspension was passed through a plug of Celite. All the volatiles were removed, and the residue was washed with diethyl ether (3×5 mL) to give 49 as a dark red powder. Yield: 68% (78.5 mg, 0.12 mmol).

$^1$H NMR (CD$_2$Cl$_2$, 300 MHz): δ 7.19 (s, 2H, CH$_{imid}$), 5.69 (d, J=5.91 Hz, 2H, CH$_{pcym}$), 5.52 (septet, J=6.60 Hz, 2H, CH$_{isop\,imid}$), 5.15 (d, J=5.88 Hz, 2H, CH$_{pcym}$), 3.29 (septet, J=6.93 Hz, 1H, CH$_{isop\,pcym}$), 2.01 (s, 3H, CH$_{3pcym}$), 1.44 (br, 12H, CH$_{3isop\,imid}$), 1.32 (d, J=6.96 Hz, 6H, CH$_{3isop\,pcym}$).

$^{13}$C NMR (CD$_2$Cl$_2$, 100 MHz): δ 167.6 (C—Ru), 120.1 (CH$_{imid}$), 108.4 (Cq$_{pcym}$), 99.8 (Cq$_{pcym}$), 87.3 (CH$_{pcym}$), 82.3 (CH$_{pcym}$), 55.0 (CH$_{isop\,imid}$), 32.0 (CH$_{isop\,pcym}$), 25.7 (CH$_{3isop\,imid}$), 25.1 (CH$_{3isop\,imid}$), 23.2 (CH$_{3isop\,pcym}$), 19.8 (CH$_{3pcym}$).

Anal. calcd for C$_{20}$H$_{32}$C$_{12}$I$_2$N2-Ru (49.3CH$_2$Cl$_2$, 726.3): C, 33.08; H, 4.44; N, 3.86. Found: C, 33.46; H, 4.01; N, 4.03.

General Procedure for Amide Synthesis using 46-50

In an argon-filled glovebox, a 10 mL oven-dried Schlenk tube was charged with complex 46, 47, 48, 49 or 50 (0.025 mmol), base (0.075 mmol), and 0.6 mL of toluene. The Schlenk tube was then taken out, and alcohol (0.50 mmol) and amine (0.55 mmol) were added. The reaction mixture was heated to reflux under a flow of argon to facilitate removal of hydrogen for 24 h before being cooled to room temperature. All the volatiles were removed under vacuum. Purification of the crude product by flash chromatography afforded amides. All the amides were identified by spectral comparison with literature data (Naota et al., 1991, supra; Watson et al., 2009, supra; Nordstroem et al., 2008, supra).

Results and Discussion of the Use of N-Heterocyclic Carbene Based Ruthenium Catalysts 46-50

Complex 48 was manufactured by modifying the reported procedure by using a Ag carbene.8 The structure was confirmed by X-ray crystallography (FIG. 13). The structure of 48 is similar to that of the reported 50. Surprisingly, when complexes 46-50 were initially screened with 2-phenylethanol and benzylamine, they did not show any activity. Mimicking the reported in situ conditions, bases such as NaH and KOtBu were found necessary for catalytic activity (FIG. 8). Weaker bases such as $K_2CO_3$ were not as effective as NaH and KOtBu (entry 11, FIG. 8). Further optimization demonstrated that only a catalytic amount of a base, 15-20 mol %, is ideal for the catalysis (FIG. 8). The major role of these bases had initially been considered for in situ generation of NHCs from imidazolium salts. However, without the intend of being bound by theory, the current results with well-defined precatalysts indicated that the role of the base is more than the mere generation of NHC. It rather appears to be related to activation of the Ru complexes. Supporting ligands such as pyridine, acetonitrile, and phosphines, which were required for improving activity of in situ generated catalysts, were not necessary for the well-defined complexes 46-50.

Interestingly, even though NHC precursors that have isopropyl wingtip groups such as 5 were reported to be significantly superior than 1,3-dimethylimidazolium salt in in situ catalyst systems (Nordstrøm et al., 2008, supra;), 46 and 48 showed comparable activity. The reason is not clear, but we think that there might be less efficiency of NHC-Ru bond formation in in situ generation with 1,3-dimethylimidazolium iodide (9).9,10 To improve the activity, we tried to exchange the chloride ligands with bromide and iodide. However, complexes 47 and 49 also did not show any improvement over 46 and 48. Synthesis of a bromo derivative of 46 and 47 was attempted; however, mixtures of mono and disubstituted bromo complexes were observed even in the presence of excess (~30 equiv) NaBr. The use of silver salts such as $AgBF_4$ to abstract chloride ligands did not show any improvement either.

Substrate Scope

Complex 46, with smaller wingtip groups of NHC, was chosen to expand the substrate scope, expecting improvement for challenging sterically hindered substrates. A range of amides were synthesized with good to excellent yields with precatalyst 46 (FIG. 9). Excellent yields were obtained for sterically nonhindered substrates (entries 1, 2). Modestly hindered substrates worked reasonably well (entries 3, 4).

Cyclic secondary amines such as 21 and 22 also reacted smoothly, producing the corresponding amides with good yields (entries 5, 6). In particular, five- to sevenmembered cyclic lactams, 29, 30, and 31, were synthesized efficiently from am-amino alcohols (entries 7-9). The electronic effect on alcohols was studied using benzyl alcohol derivatives. Slightly reduced yields were observed with electron-deficient substrates (entries 10-12). However, rather disappointingly, it also showed a similar limitation on sterically bulky substrates and less basic aniline, demonstrating challenges in this area (entries 13, 14; Gunanathan et al, 2007, supra; Naota et al., 1991, supra; Watson et al., 2009, supra; Nordstroem et al., 2008, supra).

Catalytic Intermediates

With the benefit of the structurally well-defined complex 46, an attempt was made to reveal the mechanism and catalytic intermediates during catalysis. 1-Hexanol (10) and 1-pentylamine (19) were chosen for the study, because the corresponding amide product 24 is completely soluble in toluene-$d_8$ during catalysis.

First an NMR reaction was tried with the same catalytic conditions (5 mol % 46, 15 mol % KOtBu) in toluene-$d_g$ to investigate catalytic intermediates during catalytic reactions. Several interesting features were observed. Even though complex 46 itself did not have high solubility in toluene, it was immediately solubilized by the addition of substrates in the presence of a base with characteristic peaks of π-bound p-cymene, which shows characteristic upfield shifts near 5 ppm in the $^1H$ NMR spectrum. This observation indicated that exchange of chloride with alkoxide is a rapid initiation step. Concurrent formation of ruthenium hydrides as singlets, shown at δ-6.6 ppm (major) and -7.7 ppm (minor) by $^1H$ NMR spectroscopy, was observed immediately after the addition of substrates with KOtBu at ambient temperature. When the reaction mixture was heated at 115° C. and the amide started to form, two hydridic peaks disappeared and a major hydride peak at δ-9.8 ppm was observed, along with many trace weak hydridic peaks at about δ-10 to -20 ppm (The $^1H$ NMR spectra were obtained at ambient temperature, after the NMR tube was heated at 115° C. in an oil bath for the specified time).

Further an NMR tube reaction in toluene-$d_8$ with a 1:3:3 ratio reaction of 46, 10, and KOtBu. At room temperature, a major hydride peak was observed at the same position observed in catalytic reactions at δ-6.6 ppm. However upon heating to 115° C., the hydride peak disappeared and a new singlet at δ-9.8 ppm was observed. With prolonged heating, 2-3 h, the peak disappeared along with many trace hydridic peaks, implying decomposition of catalysts. Peaks from π-bound cymene near 5-6 ppm also disappeared after a few hour heating. With 46 and 10 without a base, no reaction was observed, suggesting a base is required to generate the Ru hydride complex. These observations strongly indicated that a ruthenium hydride species is an active catalytic intermediate.

Substrate Scope

Figure 6:
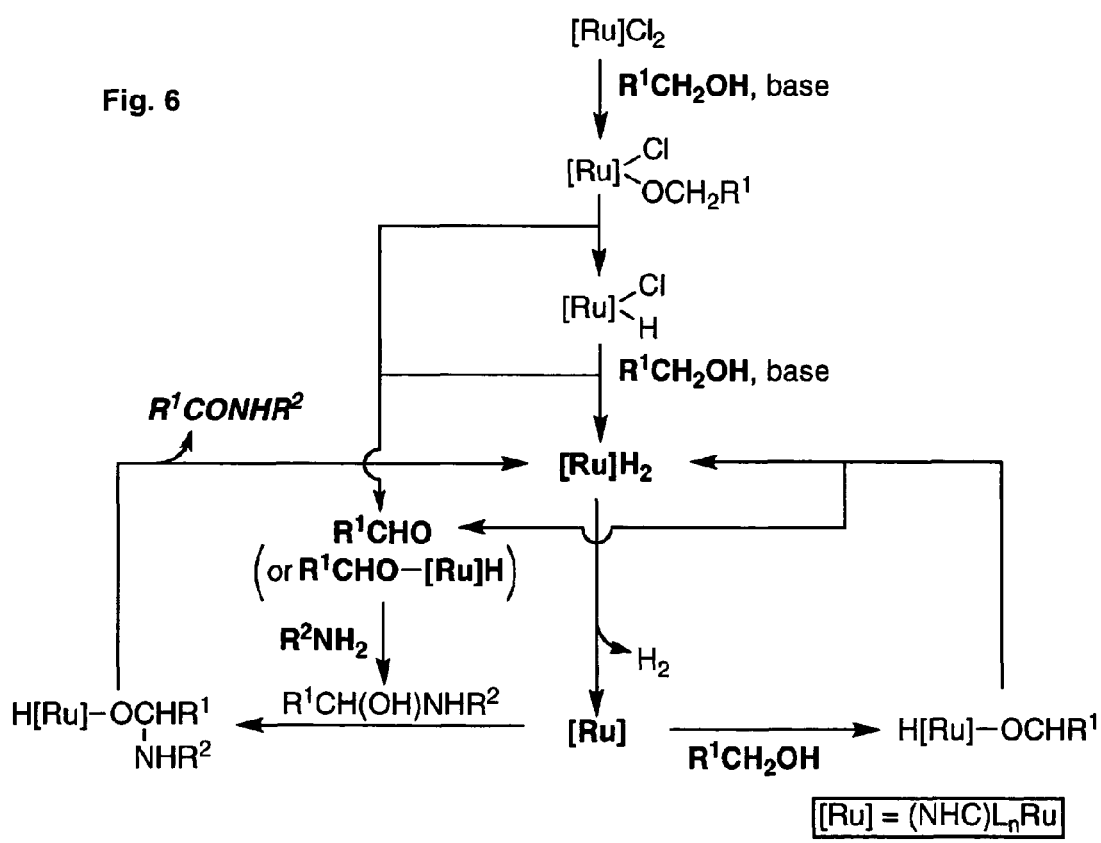
FIG. 6 illustrates, without the intent of being bound by theory, a possible reaction mechanism.
Figure 10:
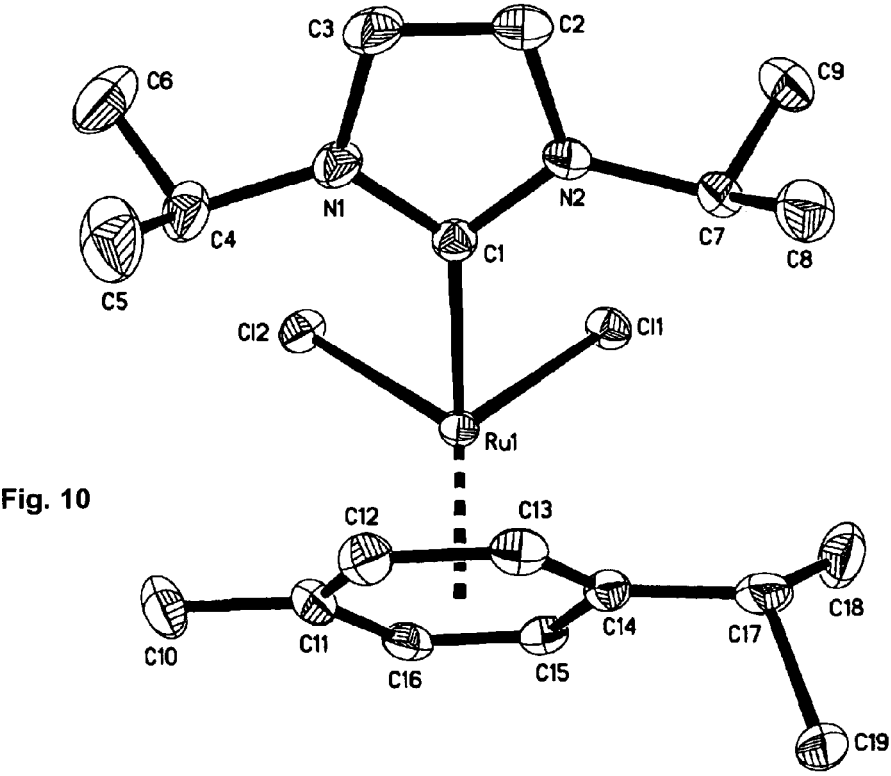
FIG. 10 depicts the crystal structure of Ruthenium (II) complex 48 with thermal ellipsoids drawn at the 50% probability level. Hydrogen atoms are omitted for clarity. Selected bond distances) (A°): Ru1-C1 2.0828(14), Ru1-Cl1 2.4439(4), Ru1-C13 2.1701(14). Selected bond angles (deg): C1-Ru1-C13 89.55(5), Cl1-Ru1-Cl1 89.87(4), Cl1-Ru1-Cl2 83.006(13).

On the basis of the studies, it is proposed that the role of a catalytic amount (at least 2 equiv vs precatalyst) of a base is to stimulate the generation of the ruthenium alkoxide species (FIG. 6). Subsequent β-hydrogen elimination can generate the Ru(II) dihydride species. The generation of [Ru]$H_2$ from [Ru]$Cl_2$ with the help of a base and the Ru(0)/Ru(II) cycle have been suggested in catalytic alcohol dehydrogenation (Zhang, J, et al., Organometallics (2004) 23, 4026), N-alkylation of amines with alcohols, and esterification of alcohols. In addition, synthesis of the [(p-cymene)RuH$_2$(PCy$_3$)] complex from [(p-cymene)RuCl$_2$(PCy$_3$)] with methanol and $K_2CO_3$ has been reported (Demerseman, B, et al., Eur. J. Inorg. Chem. (2006) 1174). However, attempts to synthesize [(p-cymene)-RuH$_2$(IMe)] 46-H$_2$ under the same conditions were not successful, limiting clear characterization of the observed Ru—H intermediate. Diminished catalytic activity from increased amount of a base from 20 mol % also supported the role of a base and implied that deprotonation of all alcohols is not necessary for alcohols to react with a catalytically active intermediate.

The proposed mechanism is similar to the mechanism proposed for the Ru-catalyzed alkylation of amine using the "borrowing hydrogen" methodology (supra). It is assumed that the critical point is whether a hemiaminal intermediate would be further oxidized to a corresponding amide or would form an imine, which could be subsequently hydrogenated to an amine by elimination of water. On the basis of the reports on the alkylation of amine done with similar Ru complexes with supporting phosphine ligands and the essential role of NHC ligands on the amide formation, it is believed that the more σ-donating NHC ligand has a critical role to facilitate the oxidation over the elimination of water.

It has been reported that in situ generated NHC-based Ru was not active (Nordstrøm et al., 2008, supra) in the amide formation of aldehydes with amines, forming imines as major products, even though aldehydes were proposed as intermediates formed by dehydrogenation of alcohols. To rationalize the results, it has been proposed that Ru coordination on the generated aldehyde would be essential for the catalytic cycle (ibid.). Indeed, no free aldehyde could be observed during the NMR studies, suggesting the short lifetime of free aldehyde, if it is generated at all.

Figure 11:
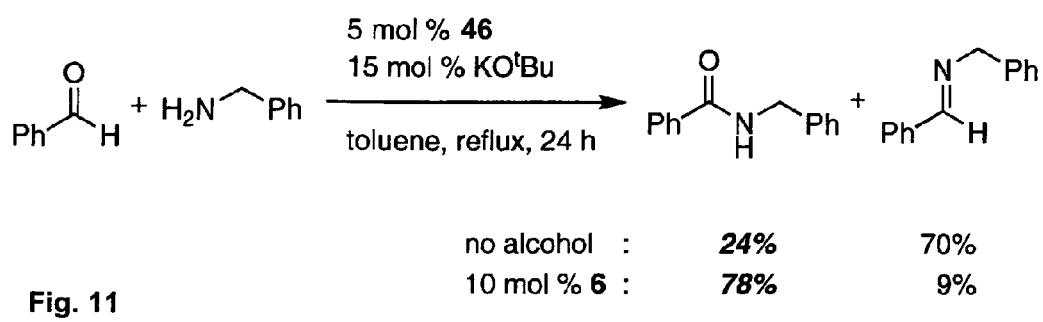
FIG. 11 shows a scheme depicting the amidation of an aldehyde as determined by gas chromatography (GC) using dodecane as an internal standard, average of two runs.

However, our study on the catalytic intermediate indicated that there might be another possible reason for the limited activity of the aldehyde. It would be less efficient to form active [Ru]H$_2$ from [Ru]Cl$_2$ and an aldehyde without the help of primary alcohols. To see whether primary alcohols are essential for the catalysis, we ran two reactions of the amidation of an aldehyde with and without a primary alcohol (FIG. 11). Aldehyde itself did not efficiently produce an amide from benzaldehyde with benzylamine under the same reaction conditions using complex 46. However, when we added 10 mol % of the primary alcohol 2-phenylethanol as an additive, the reaction smoothly generated the corresponding amide, N-benzylbenzamide, demonstrating that formation of a catalytically active species by an alcohol is necessary for the amidation of aldehydes. However, the observation of 9% of the corresponding imine (cf. FIG. 11) that was sometimes observed in trace amounts, less than 3%, in the reaction of benzyl alcohol and benzyl amine, and no observation of free aldehyde during the discussed NMR studies, implied that the direct amide formation from alcohol might occur through Ru-bound aldehyde-like species, instead of free aldehyde. A recent mechanistic study with a heterogeneous Ag catalyst on the same transformation indicated that the reaction proceeded through metal-bound aldehyde-like species, not through a free aldehyde (Shimizu, K–1, et al., Chem.: Eur. J. (2009) 15, 9977).

Figure 12:
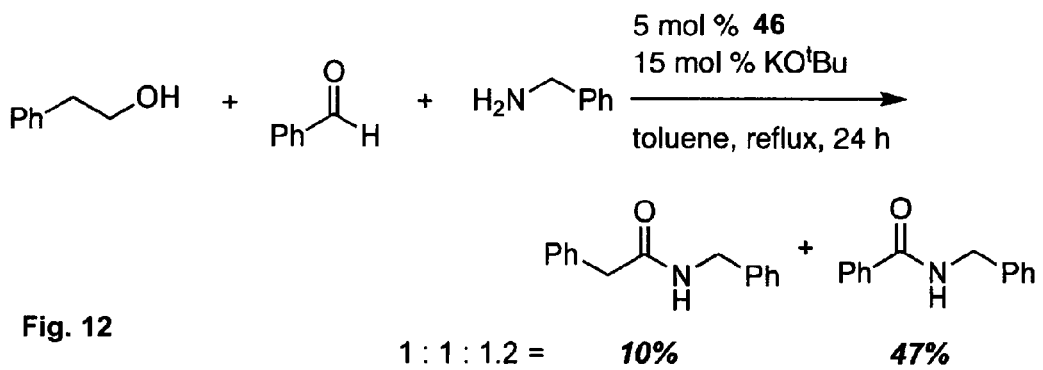
FIG. 12 shows a scheme depicting the reactions of a mixture of an alcohol and an aldehyde as determined by GC using dodecane as an internal standard, average of two runs.

To investigate further, a reaction was carried out with a mixture of 2-phenylethanol, benzaldehyde, and benzylamine (1:1:1.2 ratio). The corresponding amides N-benzyl -2-phenylacetamide and N-benzylbenzamide were obtained in 10% and 47% yields, respectively, suggesting that once a catalytically active species is generated, aldehydes could generate amides more favorably than alcohols (FIG. 12). Although it is still not conclusive whether a free aldehyde is generated during the amidation of primary alcohols or not, the present data clearly indicated that generation of a ruthenium hydride is essential for the formation of amides from either alcohol or aldehyde.

X-ray Crystallographic Data for Complex 48
Crystal Data and Structure Refinement for 48.CH$_2$Cl$_2$

| | |
|---|---|
| Empirical formula | C20 H32 Cl4 N2 Ru |
| Formula weight | 543.35 |
| Temperature | 173(2) K |
| Wavelength | 0.71073 Å |
| Crystal system | Monoclinic |
| Space group | P2(1)/n |
| Unit cell dimensions | a = 10.0156(5) Å  a= 90°. |
| | b = 17.2504(8) Å  b= 92.134(3)°. |
| | c = 13.6315(6) Å  g = 90°. |
| Volume | 2353.52(19) Å3 |
| Z | 4 |
| Density (calculated) | 1.533 Mg/m3 |
| Absorption coefficient | 1.129 mm$^{-1}$ |
| F(000) | 1112 |
| Crystal size | 0.40 × 0.24 × 0.22 mm$^3$ |
| Theta range for data collection | 1.90 to 36.40°. |
| Index ranges | −16 <= h <= 16, |
| | −28 <= k <= 27, |
| | −22 <= l <= 22 |
| Reflections collected | 82940 |
| Independent reflections | 11411 [R(int) = 0.0473] |
| Completeness to theta = 36.40° | 99.4% |
| Absorption correction | Semi-empirical from equivalents |
| Max. and min. transmission | 0.7893 and 0.6609 |
| Refinement method | Full-matrix least-squares on F$^2$ |
| Data/restraints/parameters | 11411/24/281 |
| Goodness-of-fit on F$^2$ | 1.089 |
| Final R indices [I > 2sigma(I)] | R1 = 0.0293, wR2 = 0.0749 |
| R indices (all data) | R1 = 0.0441, wR2 = 0.0856 |
| Largest diff. peak and hole | 0.805 and −0.689 e.Å$^{-3}$ |

Atomic Coordinates (×104) and Equivalent Isotropic Displacement Parameters (Å2×10$^3$) for 48. U(eq) is Defined as One Third of the Trace of the Orthogonalized U$^{ij}$ Tensor.

| | x | y | z | U(eq) |
|---|---|---|---|---|
| Ru(1) | 4521(1) | 948(1) | 8289(1) | 15(1) |
| C(1) | 4872(1) | 1873(1) | 7351(1) | 18(1) |
| C(2) | 4638(2) | 2973(1) | 6456(1) | 28(1) |
| C(3) | 5819(2) | 2657(1) | 6238(1) | 29(1) |
| C(4) | 7056(2) | 1440(1) | 6626(1) | 29(1) |
| C(5) | 6957(2) | 1128(2) | 5581(2) | 46(1) |
| C(6) | 8383(2) | 1848(2) | 6838(2) | 45(1) |
| C(7) | 2717(2) | 2638(1) | 7495(1) | 21(1) |
| C(8) | 1687(2) | 2625(1) | 6643(1) | 30(1) |
| C(9) | 2694(2) | 3404(1) | 8046(1) | 29(1) |
| C(10) | 6404(2) | −617(1) | 7797(2) | 39(1) |
| C(11) | 5050(2) | −255(1) | 7887(1) | 24(1) |
| C(12) | 4388(2) | 116(1) | 7086(1) | 24(1) |
| C(13) | 3113(2) | 470(1) | 7202(1) | 22(1) |
| C(14) | 2481(1) | 448(1) | 8111(1) | 19(1) |
| C(15) | 3155(1) | 48(1) | 8904(1) | 20(1) |
| C(16) | 4395(2) | −299(1) | 8797(1) | 22(1) |
| C(17) | 1105(12) | 768(8) | 8218(10) | 34(3) |
| C(18) | 729(7) | 1136(7) | 9119(6) | 37(1) |
| C(19) | 18(14) | 149(7) | 7875(12) | 33(2) |
| C(17A) | 1039(13) | 761(9) | 8158(11) | 20(2) |
| C(18A) | 711(10) | 869(13) | 9322(12) | 48(3) |
| C(19A) | 149(19) | 160(11) | 7726(17) | 42(4) |
| C(20) | 1705(2) | 1778(2) | 4122(2) | 48(1) |
| Cl(1) | 3952(1) | 1861(1) | 9579(1) | 21(1) |
| Cl(2) | 6778(1) | 1124(1) | 8983(1) | 22(1) |
| Cl(3) | 3416(1) | 1811(1) | 4450(1) | 69(1) |
| Cl(4) | 926(1) | 970(1) | 4663(1) | 63(1) |
| N(1) | 5946(1) | 1982(1) | 6781(1) | 23(1) |
| N(2) | 4065(1) | 2488(1) | 7132(1) | 20(1) |

Bond lengths [Å] and angles [°] for 48

| | |
|---|---|
| Ru(1)—C(1) | 2.0828(14) |
| Ru(1)—C(13) | 2.1701(14) |
| Ru(1)—C(12) | 2.1799(15) |
| Ru(1)—C(11) | 2.2151(16) |
| Ru(1)—C(14) | 2.2231(14) |
| Ru(1)—C(15) | 2.2525(14) |
| Ru(1)—C(16) | 2.2657(15) |
| Ru(1)—Cl(2) | 2.4365(4) |
| Ru(1)—Cl(1) | 2.4439(4) |
| C(1)—N(2) | 1.3599(19) |
| C(1)—N(1) | 1.3632(18) |
| C(2)—C(3) | 1.345(2) |
| C(2)—N(2) | 1.3856(19) |
| C(2)—H(2) | 0.9500 |
| C(3)—N(1) | 1.383(2) |
| C(3)—H(3) | 0.9500 |
| C(4)—N(1) | 1.475(2) |
| C(4)—C(6) | 1.521(3) |
| C(4)—C(5) | 1.523(3) |
| C(4)—H(4) | 1.0000 |
| C(5)—H(5A) | 0.9800 |
| C(5)—H(5B) | 0.9800 |
| C(5)—H(5C) | 0.9800 |
| C(6)—H(6A) | 0.9800 |
| C(6)—H(6B) | 0.9800 |
| C(6)—H(6C) | 0.9800 |
| C(7)—N(2) | 1.4779(19) |
| C(7)—C(9) | 1.522(2) |
| C(7)—C(8) | 1.525(2) |

| | |
|---|---|
| C(7)—H(7) | 1.0000 |
| C(8)—H(8A) | 0.9800 |
| C(8)—H(8B) | 0.9800 |
| C(8)—H(8C) | 0.9800 |
| C(9)—H(9A) | 0.9800 |
| C(9)—H(9B) | 0.9800 |
| C(9)—H(9C) | 0.9800 |
| C(10)—C(11) | 1.502(2) |
| C(10)—H(10A) | 0.9800 |
| C(10)—H(10B) | 0.9800 |
| C(10)—H(10C) | 0.9800 |
| C(11)—C(12) | 1.409(2) |
| C(11)—C(16) | 1.427(2) |
| C(12)—C(13) | 1.430(2) |
| C(12)—H(12) | 1.0000 |
| C(13)—C(14) | 1.413(2) |
| C(13)—H(13) | 1.0000 |
| C(14)—C(15) | 1.431(2) |
| C(14)—C(17) | 1.497(11) |
| C(14)—C(17A) | 1.545(12) |
| C(15)—C(16) | 1.392(2) |
| C(15)—H(15) | 1.0000 |
| C(16)—H(16) | 1.0000 |
| C(17)—C(18) | 1.445(14) |
| C(17)—C(19) | 1.583(18) |
| C(17)—H(17) | 1.0000 |
| C(18)—H(18A) | 0.9800 |
| C(18)—H(18B) | 0.9800 |
| C(18)—H(18C) | 0.9800 |
| C(19)—H(19A) | 0.9800 |
| C(19)—H(19B) | 0.9800 |
| C(19)—H(19C) | 0.9800 |
| C(17A)—C(19A) | 1.48(2) |
| C(17A)—C(18A) | 1.64(2) |
| C(17A)—H(17A) | 1.0000 |
| C(18A)—H(18D) | 0.9800 |
| C(18A)—H(18E) | 0.9800 |
| C(18A)—H(18F) | 0.9800 |
| C(19A)—H(19D) | 0.9800 |
| C(19A)—H(19E) | 0.9800 |
| C(19A)—H(19F) | 0.9800 |
| C(20)—Cl(3) | 1.756(2) |
| C(20)—Cl(4) | 1.772(3) |
| C(20)—H(20A) | 0.9900 |
| C(20)—H(20B) | 0.9900 |
| C(1)—Ru(1)—C(13) | 89.55(5) |
| C(1)—Ru(1)—C(12) | 92.87(6) |
| C(13)—Ru(1)—C(12) | 38.38(6) |
| C(1)—Ru(1)—C(11) | 121.24(6) |
| C(13)—Ru(1)—C(11) | 68.32(6) |
| C(12)—Ru(1)—C(11) | 37.40(6) |
| C(1)—Ru(1)—C(14) | 113.92(5) |
| C(13)—Ru(1)—C(14) | 37.49(5) |
| C(12)—Ru(1)—C(14) | 68.40(6) |
| C(11)—Ru(1)—C(14) | 80.61(6) |
| C(1)—Ru(1)—C(15) | 151.09(5) |
| C(13)—Ru(1)—C(15) | 66.66(5) |
| C(12)—Ru(1)—C(15) | 78.76(6) |
| C(11)—Ru(1)—C(15) | 66.48(6) |
| C(14)—Ru(1)—C(15) | 37.27(5) |
| C(1)—Ru(1)—C(16) | 158.12(6) |
| C(13)—Ru(1)—C(16) | 78.77(6) |
| C(12)—Ru(1)—C(16) | 66.51(6) |
| C(11)—Ru(1)—C(16) | 37.11(6) |
| C(14)—Ru(1)—C(16) | 66.61(5) |
| C(15)—Ru(1)—C(16) | 35.88(5) |
| C(1)—Ru(1)—Cl(2) | 88.17(4) |
| C(13)—Ru(1)—Cl(2) | 151.95(4) |
| C(12)—Ru(1)—Cl(2) | 113.85(4) |
| C(11)—Ru(1)—Cl(2) | 89.19(4) |
| C(14)—Ru(1)—Cl(2) | 157.87(4) |
| C(15)—Ru(1)—Cl(2) | 120.59(4) |
| C(16)—Ru(1)—Cl(2) | 93.52(4) |
| C(1)—Ru(1)—Cl(1) | 89.87(4) |
| C(13)—Ru(1)—Cl(1) | 124.95(4) |
| C(12)—Ru(1)—Cl(1) | 162.99(4) |
| C(11)—Ru(1)—Cl(1) | 147.73(4) |
| C(14)—Ru(1)—Cl(1) | 95.17(4) |
| C(15)—Ru(1)—Cl(1) | 90.81(4) |
| C(16)—Ru(1)—Cl(1) | 111.99(4) |
| Cl(2)—Ru(1)—Cl(1) | 83.006(13) |
| N(2)—C(1)—N(1) | 104.03(12) |
| N(2)—C(1)—Ru(1) | 128.31(10) |
| N(1)—C(1)—Ru(1) | 127.61(11) |
| C(3)—C(2)—N(2) | 106.96(14) |
| C(3)—C(2)—H(2) | 126.5 |
| N(2)—C(2)—H(2) | 126.5 |
| C(2)—C(3)—N(1) | 106.68(13) |
| C(2)—C(3)—H(3) | 126.7 |
| N(1)—C(3)—H(3) | 126.7 |
| N(1)—C(4)—C(6) | 109.72(17) |
| N(1)—C(4)—C(5) | 109.57(15) |
| C(6)—C(4)—C(5) | 111.57(16) |
| N(1)—C(4)—H(4) | 108.6 |
| C(6)—C(4)—H(4) | 108.6 |
| C(5)—C(4)—H(4) | 108.6 |
| C(4)—C(5)—H(5A) | 109.5 |
| C(4)—C(5)—H(5B) | 109.5 |
| H(5A)—C(5)—H(5B) | 109.5 |
| C(4)—C(5)—H(5C) | 109.5 |
| H(5A)—C(5)—H(5C) | 109.5 |
| H(5B)—C(5)—H(5C) | 109.5 |
| C(4)—C(6)—H(6A) | 109.5 |
| C(4)—C(6)—H(6B) | 109.5 |
| H(6A)—C(6)—H(6B) | 109.5 |
| C(4)—C(6)—H(6C) | 109.5 |
| H(6A)—C(6)—H(6C) | 109.5 |
| H(6B)—C(6)—H(6C) | 109.5 |
| N(2)—C(7)—C(9) | 110.36(13) |
| N(2)—C(7)—C(8) | 110.06(13) |
| C(9)—C(7)—C(8) | 111.52(13) |
| N(2)—C(7)—H(7) | 108.3 |
| C(9)—C(7)—H(7) | 108.3 |
| C(8)—C(7)—H(7) | 108.3 |
| C(7)—C(8)—H(8A) | 109.5 |
| C(7)—C(8)—H(8B) | 109.5 |
| H(8A)—C(8)—H(8B) | 109.5 |
| C(7)—C(8)—H(8C) | 109.5 |
| H(8A)—C(8)—H(8C) | 109.5 |
| H(8B)—C(8)—H(8C) | 109.5 |
| C(7)—C(9)—H(9A) | 109.5 |
| C(7)—C(9)—H(9B) | 109.5 |
| H(9A)—C(9)—H(9B) | 109.5 |
| C(7)—C(9)—H(9C) | 109.5 |
| H(9A)—C(9)—H(9C) | 109.5 |
| H(9B)—C(9)—H(9C) | 109.5 |
| C(11)—C(10)—H(10A) | 109.5 |
| C(11)—C(10)—H(10B) | 109.5 |
| H(10A)—C(10)—H(10B) | 109.5 |
| C(11)—C(10)—H(10C) | 109.5 |
| H(10A)—C(10)—H(10C) | 109.5 |
| H(10B)—C(10)—H(10C) | 109.5 |
| C(12)—C(11)—C(16) | 118.63(14) |
| C(12)—C(11)—C(10) | 121.72(16) |
| C(16)—C(11)—C(10) | 119.63(16) |
| C(12)—C(11)—Ru(1) | 69.95(9) |
| C(16)—C(11)—Ru(1) | 73.37(9) |
| C(10)—C(11)—Ru(1) | 129.39(12) |
| C(11)—C(12)—C(13) | 120.32(13) |
| C(11)—C(12)—Ru(1) | 72.66(9) |
| C(13)—C(12)—Ru(1) | 70.44(8) |
| C(11)—C(12)—H(12) | 119.3 |
| C(13)—C(12)—H(12) | 119.3 |
| Ru(1)—C(12)—H(12) | 119.3 |
| C(14)—C(13)—C(12) | 121.10(13) |
| C(14)—C(13)—Ru(1) | 73.29(8) |
| C(12)—C(13)—Ru(1) | 71.18(8) |
| C(14)—C(13)—H(13) | 119.0 |
| C(12)—C(13)—H(13) | 119.0 |
| Ru(1)—C(13)—H(13) | 119.0 |
| C(13)—C(14)—C(15) | 117.52(13) |
| C(13)—C(14)—C(17) | 121.3(6) |
| C(15)—C(14)—C(17) | 120.9(6) |
| C(16)—Ru(1)—Cl(1) | 111.99(4) |
| Cl(2)—Ru(1)—Cl(1) | 83.006(13) |
| N(2)—C(1)—N(1) | 104.03(12) |
| N(2)—C(1)—Ru(1) | 128.31(10) |
| N(1)—C(1)—Ru(1) | 127.61(11) |

| | |
|---|---|
| C(3)—C(2)—N(2) | 106.96(14) |
| C(3)—C(2)—H(2) | 126.5 |
| N(2)—C(2)—H(2) | 126.5 |
| C(2)—C(3)—N(1) | 106.68(13) |
| C(2)—C(3)—H(3) | 126.7 |
| N(1)—C(3)—H(3) | 126.7 |
| N(1)—C(4)—C(6) | 109.72(17) |
| N(1)—C(4)—C(5) | 109.57(15) |
| C(6)—C(4)—C(5) | 111.57(16) |
| N(1)—C(4)—H(4) | 108.6 |
| C(6)—C(4)—H(4) | 108.6 |
| C(5)—C(4)—H(4) | 108.6 |
| C(4)—C(5)—H(5A) | 109.5 |
| C(4)—C(5)—H(5B) | 109.5 |
| H(5A)—C(5)—H(5B) | 109.5 |
| C(4)—C(5)—H(5C) | 109.5 |
| H(5A)—C(5)—H(5C) | 109.5 |
| H(5B)—C(5)—H(5C) | 109.5 |
| C(4)—C(6)—H(6A) | 109.5 |
| C(4)—C(6)—H(6B) | 109.5 |
| H(6A)—C(6)—H(6B) | 109.5 |
| C(4)—C(6)—H(6C) | 109.5 |
| H(6A)—C(6)—H(6C) | 109.5 |
| H(6B)—C(6)—H(6C) | 109.5 |
| N(2)—C(7)—C(9) | 110.36(13) |
| N(2)—C(7)—C(8) | 110.06(13) |
| C(9)—C(7)—C(8) | 111.52(13) |
| N(2)—C(7)—H(7) | 108.3 |
| C(9)—C(7)—H(7) | 108.3 |
| C(8)—C(7)—H(7) | 108.3 |
| C(7)—C(8)—H(8A) | 109.5 |
| C(7)—C(8)—H(8B) | 109.5 |
| H(8A)—C(8)—H(8B) | 109.5 |
| C(7)—C(8)—H(8C) | 109.5 |
| H(8A)—C(8)—H(8C) | 109.5 |
| H(8B)—C(8)—H(8C) | 109.5 |
| C(7)—C(9)—H(9A) | 109.5 |
| C(7)—C(9)—H(9B) | 109.5 |
| H(9A)—C(9)—H(9B) | 109.5 |
| C(7)—C(9)—H(9C) | 109.5 |
| H(9A)—C(9)—H(9C) | 109.5 |
| H(9B)—C(9)—H(9C) | 109.5 |
| C(11)—C(10)—H(10A) | 109.5 |
| C(11)—C(10)—H(10B) | 109.5 |
| H(10A)—C(10)—H(10B) | 109.5 |
| C(11)—C(10)—H(10C) | 109.5 |
| H(10A)—C(10)—H(10C) | 109.5 |
| H(10B)—C(10)—H(10C) | 109.5 |
| C(12)—C(11)—C(16) | 118.63(14) |
| C(12)—C(11)—C(10) | 121.72(16) |
| C(16)—C(11)—C(10) | 119.63(16) |
| C(12)—C(11)—Ru(1) | 69.95(9) |
| C(16)—C(11)—Ru(1) | 73.37(9) |
| C(10)—C(11)—Ru(1) | 129.39(12) |
| C(11)—C(12)—C(13) | 120.32(13) |
| C(11)—C(12)—Ru(1) | 72.66(9) |
| C(13)—C(12)—Ru(1) | 70.44(8) |
| C(11)—C(12)—H(12) | 119.3 |
| C(13)—C(12)—H(12) | 119.3 |
| Ru(1)—C(12)—H(12) | 119.3 |
| C(14)—C(13)—C(12) | 121.10(13) |
| C(14)—C(13)—Ru(1) | 73.29(8) |
| C(12)—C(13)—Ru(1) | 71.18(8) |
| C(14)—C(13)—H(13) | 119.0 |
| C(12)—C(13)—H(13) | 119.0 |
| Ru(1)—C(13)—H(13) | 119.0 |
| C(13)—C(14)—C(15) | 117.52(13) |
| C(13)—C(14)—C(17) | 121.3(6) |
| C(15)—C(14)—C(17) | 120.9(6) |
| C(13)—C(14)—C(17A) | 118.5(6) |
| C(15)—C(14)—C(17A) | 123.5(6) |
| C(17)—C(14)—C(17A) | 3.5(11) |
| C(13)—C(14)—Ru(1) | 69.22(8) |
| C(15)—C(14)—Ru(1) | 72.48(8) |
| C(17)—C(14)—Ru(1) | 133.8(5) |
| C(17A)—C(14)—Ru(1) | 135.8(6) |
| C(16)—C(15)—C(14) | 121.70(13) |
| C(16)—C(15)—Ru(1) | 72.58(8) |
| C(14)—C(15)—Ru(1) | 70.25(8) |
| C(16)—C(15)—H(15) | 118.4 |
| C(14)—C(15)—H(15) | 118.4 |
| Ru(1)—C(15)—H(15) | 118.4 |
| C(15)—C(16)—C(11) | 120.66(13) |
| C(15)—C(16)—Ru(1) | 71.54(8) |
| C(11)—C(16)—Ru(1) | 69.52(9) |
| C(15)—C(16)—H(16) | 118.8 |
| C(11)—C(16)—H(16) | 118.8 |
| Ru(1)—C(16)—H(16) | 118.8 |
| C(18)—C(17)—C(14) | 121.0(10) |
| C(18)—C(17)—C(19) | 110.5(9) |
| C(14)—C(17)—C(19) | 110.4(9) |
| C(18)—C(17)—H(17) | 104.5 |
| C(14)—C(17)—H(17) | 104.5 |
| C(19)—C(17)—H(17) | 104.5 |
| C(19A)—C(17A)—C(14) | 106.9(11) |
| C(19A)—C(17A)—C(18A) | 109.0(12) |
| C(14)—C(17A)—C(18A) | 107.5(12) |
| C(19A)—C(17A)—H(17A) | 111.1 |
| C(14)—C(17A)—H(17A) | 111.1 |
| C(18A)—C(17A)—H(17A) | 111.1 |
| C(17A)—C(18A)—H(18D) | 109.5 |
| C(17A)—C(18A)—H(18E) | 109.5 |
| H(18D)—C(18A)—H(18E) | 109.5 |
| C(17A)—C(18A)—H(18F) | 109.5 |
| H(18D)—C(18A)—H(18F) | 109.5 |
| H(18E)—C(18A)—H(18F) | 109.5 |
| C(17A)—C(19A)—H(19D) | 109.5 |
| C(17A)—C(19A)—H(19E) | 109.5 |
| H(19D)—C(19A)—H(19E) | 109.5 |
| C(17A)—C(19A)—H(19F) | 109.5 |
| H(19D)—C(19A)—H(19F) | 109.5 |
| H(19E)—C(19A)—H(19F) | 109.5 |
| Cl(3)—C(20)—Cl(4) | 111.06(13) |
| Cl(3)—C(20)—H(20A) | 109.4 |
| Cl(4)—C(20)—H(20A) | 109.4 |
| Cl(3)—C(20)—H(20B) | 109.4 |
| Cl(4)—C(20)—H(20B) | 109.4 |
| H(20A)—C(20)—H(20B) | 108.0 |
| C(1)—N(1)—C(3) | 111.26(13) |
| C(1)—N(1)—C(4) | 127.55(13) |
| C(3)—N(1)—C(4) | 120.81(13) |
| C(1)—N(2)—C(2) | 111.06(12) |
| C(1)—N(2)—C(7) | 127.28(12) |
| C(2)—N(2)—C(7) | 121.60(13) |

Anisotropic displacement parameters (Å²×10³) for 48

The Anisotropic Displacement Factor Exponent takes the Form: $-2p^2[h^2a^{*2}U^{11} + \ldots + 2hk\, a^*b^*U^{12}]$

| | $U^{11}$ | $U^{22}$ | $U^{33}$ | $U^{23}$ | $U^{13}$ | $U^{12}$ |
|---|---|---|---|---|---|---|
| Ru(1) | 16(1) | 14(1) | 14(1) | 2(1) | 1(1) | 0(1) |
| C(1) | 19(1) | 17(1) | 18(1) | 2(1) | 1(1) | −1(1) |
| C(2) | 32(1) | 21(1) | 29(1) | 11(1) | 5(1) | −1(1) |
| C(3) | 29(1) | 28(1) | 29(1) | 13(1) | 6(1) | −2(1) |
| C(4) | 24(1) | 36(1) | 28(1) | 11(1) | 9(1) | 7(1) |
| C(5) | 55(1) | 54(1) | 32(1) | 6(1) | 20(1) | 15(1) |
| C(6) | 22(1) | 61(2) | 53(1) | 30(1) | 4(1) | −1(1) |
| C(7) | 22(1) | 18(1) | 25(1) | 3(1) | 2(1) | 3(1) |
| C(8) | 27(1) | 29(1) | 33(1) | 2(1) | −6(1) | 2(1) |
| C(9) | 36(1) | 21(1) | 31(1) | −2(1) | 2(1) | 6(1) |
| C(10) | 29(1) | 30(1) | 58(1) | −12(1) | 5(1) | 9(1) |
| C(11) | 24(1) | 18(1) | 32(1) | −5(1) | 2(1) | 1(1) |
| C(12) | 29(1) | 25(1) | 20(1) | −5(1) | 5(1) | −4(1) |
| C(13) | 28(1) | 20(1) | 18(1) | 0(1) | −4(1) | −4(1) |
| C(14) | 19(1) | 17(1) | 23(1) | 0(1) | −1(1) | −2(1) |
| C(15) | 23(1) | 18(1) | 20(1) | 3(1) | 2(1) | −5(1) |
| C(16) | 26(1) | 14(1) | 26(1) | 3(1) | −4(1) | −2(1) |
| C(17) | 26(3) | 18(4) | 57(5) | −3(3) | −8(3) | −7(3) |
| C(18) | 22(2) | 44(4) | 43(3) | −5(2) | 9(2) | 2(2) |
| C(19) | 20(3) | 23(3) | 55(5) | −13(3) | −1(2) | −5(2) |
| C(17A) | 10(2) | 23(5) | 27(3) | −2(3) | 1(2) | 6(3) |
| C(18A) | 30(3) | 63(7) | 52(5) | −18(5) | 18(3) | −5(4) |
| C(19A) | 12(3) | 37(5) | 75(9) | 10(5) | −4(4) | −1(2) |
| C(20) | 51(1) | 51(1) | 43(1) | −10(1) | −11(1) | 17(1) |

-continued

|       | $U^{11}$ | $U^{22}$ | $U^{33}$ | $U^{23}$ | $U^{13}$ | $U^{12}$ |
|-------|------|------|------|------|------|------|
| Cl(1) | 26(1) | 18(1) | 18(1) | −2(1) | 2(1) | 0(1) |
| Cl(2) | 18(1) | 25(1) | 22(1) | 6(1) | −2(1) | −2(1) |
| Cl(3) | 50(1) | 92(1) | 64(1) | −26(1) | −12(1) | 14(1) |
| Cl(4) | 75(1) | 46(1) | 66(1) | −7(1) | −22(1) | 5(1) |
| N(1)  | 21(1) | 24(1) | 23(1) | 8(1) | 4(1) | −1(1) |
| N(2)  | 22(1) | 16(1) | 22(1) | 5(1) | 2(1) | 1(1) |

Hydrogen Coordinates ($\times 10^4$) and Isotropic Displacement Parameters ($Å^2 \times 10^3$) for 48

|        | x    | y    | z    | U(eq) |
|--------|------|------|------|-------|
| H(2)   | 4268 | 3441 | 6196 | 33 |
| H(3)   | 6444 | 2859 | 5796 | 34 |
| H(4)   | 6981 | 996  | 7092 | 35 |
| H(5A)  | 6059 | 918  | 5447 | 69 |
| H(5B)  | 7620 | 716  | 5506 | 69 |
| H(5C)  | 7127 | 1548 | 5118 | 69 |
| H(6A)  | 8439 | 2309 | 6421 | 68 |
| H(6B)  | 9118 | 1495 | 6700 | 68 |
| H(6C)  | 8445 | 2003 | 7529 | 68 |
| H(7)   | 2494 | 2214 | 7962 | 25 |
| H(8A)  | 1882 | 3041 | 6181 | 45 |
| H(8B)  | 792  | 2701 | 6895 | 45 |
| H(8C)  | 1724 | 2123 | 6307 | 45 |
| H(9A)  | 3349 | 3389 | 8598 | 44 |
| H(9B)  | 1800 | 3491 | 8295 | 44 |
| H(9C)  | 2917 | 3827 | 7601 | 44 |
| H(10A) | 6308 | −1180 | 7738 | 59 |
| H(10B) | 6962 | −494 | 8382 | 59 |
| H(10C) | 6825 | −412 | 7213 | 59 |
| H(12)  | 4884 | 218  | 6476 | 29 |
| H(13)  | 2740 | 815  | 6669 | 26 |
| H(15)  | 2831 | 125  | 9583 | 24 |
| H(16)  | 4924 | −461 | 9399 | 27 |
| H(17)  | 1025 | 1188 | 7714 | 41 |
| H(18A) | 765  | 756  | 9653 | 55 |
| H(18B) | −181 | 1341 | 9039 | 55 |
| H(18C) | 1349 | 1562 | 9277 | 55 |
| H(19A) | 82   | −305 | 8306 | 49 |
| H(19B) | 174  | −8   | 7198 | 49 |
| H(19C) | −875 | 378  | 7909 | 49 |
| H(17A) | 937  | 1262 | 7794 | 24 |
| H(18D) | −108 | 1175 | 9377 | 72 |
| H(18E) | 1456 | 1139 | 9661 | 72 |
| H(18F) | 589  | 359  | 9622 | 72 |
| H(19D) | 312  | 108  | 7024 | 62 |
| H(19E) | −784 | 308  | 7811 | 62 |
| H(19F) | 329  | −336 | 8055 | 62 |
| H(20A) | 1589 | 1745 | 3399 | 58 |
| H(20B) | 1271 | 2261 | 4339 | 58 |

CONCLUSIONS

An improved method for the amidation of amines with alcohols or aldehydes using commercially available ruthenium complexes such as the economical ruthenium trichloride ($RuCl_3$), an N-heterocyclic carbene (NHC) ligand, and the economical pyridine or acetonitrile ligand has been demonstrated. The phosphine-free process will provide alternative opportunities for the preparation of the fundamental amide functional group.

In situ generated ruthenium catalysts (from readily available ruthenium sources, such as $RuCl_3$, $RuH_2(PR_3)_4$, [Ru(p-cymene)$Cl_2$]$_2$, [Ru(benzene)$Cl_2$]$_2$, $RuH(Cl)(CO)(PR_3)_3$, $RuH_2(CO)(PR_3)_3$, etc, with N-heterocyclic carbene ligands, L-type nitrogen containing ligands, and base) have been developed for the amide synthesis from alcohols or aldehydes with amines. These economical catalyst systems show efficient conversion toward the amides.

Without being bound by theory, (arene)Ru(NHC)$X_2$ type catalysts can be applied in the amide synthesis. These catalysts work efficiently on the amide synthesis reactions, such as N-benzyl-2-phenylacetamide synthesis from 2-phenyl ethanol with benzyl amine, with help of bases. The above data further demonstrate that well-defined N-heterocyclic carbene based ruthenium complexes are active for the direct amide synthesis of alcohols with a catalytic amount of a base.

A process according to the invention, involving a ruthenium (II) catalyst as described above, is economical and simple compared to the already commercialized Milstein catalyst (CAS 893671-63-5, Strem #44-0091, USD $380/500 mg).

The Ru complexes allowed approaching a facile mechanistic investigation. The results suggest that the formation of a Ru hydride catalytic intermediate by the respective alcohol and a catalytic amount of the base is necessary for catalytic cycles.

The listing or discussion of a previously published document in this specification should not necessarily be taken as an acknowledgement that the document is part of the state of the art or is common general knowledge.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The molecular complexes and the methods, procedures, treatments, molecules, specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" etc. shall be read expansively and without limitation, and are not limited to only the listed components they directly reference, but include also other non-specified components or elements. As such they may be exchanged with each other. Additionally, the terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A process of forming an amide, the process comprising:
providing a Ruthenium (II) catalyst, the Ruthenium (II) catalyst being free of a phosphine ligand, wherein providing the Ruthenium (II) catalyst comprises:
providing an N-heterocyclic carbene formed from an imidazole or an imidazoline compound and a base, wherein the imidazole compound is of general formula (I) and the imidazoline compound is of general formula (II):

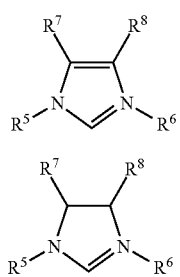

wherein $R^5$-$R^8$ are independently H, alkyl or aryl; and
contacting the N-heterocyclic carbene with a [Ru(A)Cl$_2$]$_2$ precatalyst complex, wherein A in [Ru(A)Cl$_2$]$_2$ is a benzene based moiety of general formula (III)

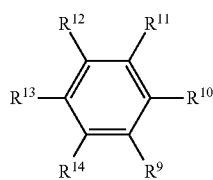

wherein $R^9$-$R^{14}$ are independently H, alkyl, or aryl; and
contacting in the presence of the Ruthenium (II) catalyst a primary or a secondary amine and a primary alcohol, wherein the primary or secondary amine and the primary alcohol are (i) a primary or secondary amine moiety of a first reactant and a primary alcohol moiety of a second reactant, or (ii) a first moiety, being a primary or secondary amine, and a second moiety, being a primary alcohol, of the same compound,
wherein the process is carried out without adding a phosphine.

2. The process of claim 1, wherein the primary or a secondary amine and the primary alcohol are moieties of the same compound and wherein the process is a process of forming a lactam.

3. The process of claim 1, wherein the N-heterocyclic carbene is provided as a complex with a metal halogenide.

4. The process of claim 1, wherein the Ruthenium (II) catalyst is formed *in situ* from the N-heterocyclic carbene and the [Ru(A)Cl$_2$]$_2$ precatalyst complex in the presence of the base.

5. The process of claim 1, wherein providing the Ruthenium (II) catalyst comprises forming one or more Ruthenium (II) complexes of formulae (IV)

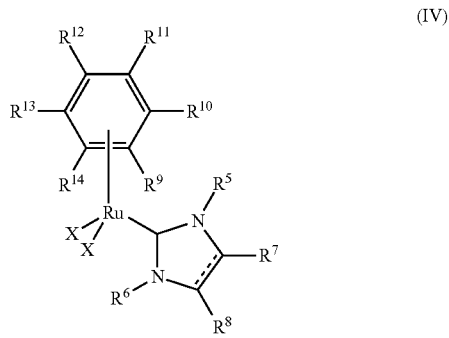

wherein:
⚌ represents one of a single and a double bond;
$R^5$-$R^{14}$ are independently H, alkyl or aryl;
X is Cl.

* * * * *